(12) United States Patent
Bremel et al.

(10) Patent No.: US 10,799,582 B2
(45) Date of Patent: Oct. 13, 2020

(54) IMMUNOGLOBULIN POLYPEPTIDE FRACTIONS FROM PRODUCTS OF DOMESTIC ANIMALS

(71) Applicant: IOGENETICS, LLC, Madison, WI (US)

(72) Inventors: Robert D. Bremel, Hillpoint, WI (US); Jane Homan, Hillpoint, WI (US)

(73) Assignee: IOGENETICS, LLC, Madison, WI (US)

( * ) Notice: Subject to any disclaimer, the term of this patent is extended or adjusted under 35 U.S.C. 154(b) by 328 days.

(21) Appl. No.: 15/325,654

(22) PCT Filed: Jul. 10, 2015

(86) PCT No.: PCT/US2015/039970
§ 371 (c)(1),
(2) Date: Jan. 11, 2017

(87) PCT Pub. No.: WO2016/007871
PCT Pub. Date: Jan. 14, 2016

(65) Prior Publication Data
US 2018/0221474 A1 Aug. 9, 2018

Related U.S. Application Data

(60) Provisional application No. 62/023,220, filed on Jul. 11, 2014, provisional application No. 62/138,460, filed on Mar. 26, 2015.

(51) Int. Cl.
*A61K 39/395* (2006.01)
*C07K 16/00* (2006.01)
*A61K 9/00* (2006.01)
*C07K 16/04* (2006.01)

(52) U.S. Cl.
CPC ...... *A61K 39/39508* (2013.01); *A61K 9/0053* (2013.01); *A61K 39/39583* (2013.01); *A61K 39/39591* (2013.01); *C07K 16/00* (2013.01); *C07K 16/04* (2013.01); *C07K 2317/12* (2013.01); *C07K 2317/20* (2013.01); *C07K 2317/21* (2013.01); *C07K 2317/24* (2013.01); *C07K 2317/56* (2013.01); *C07K 2317/94* (2013.01)

(58) Field of Classification Search
None
See application file for complete search history.

(56) References Cited

FOREIGN PATENT DOCUMENTS

WO 98/52976 11/1998

OTHER PUBLICATIONS

Mee, John F., et al. "Effect of a whey protein concentrate used as a colostrum substitute or supplement on calf immunity, weight gain, and health." Journal of dairy science 79.5 (1996): 886-894.*
European Search Report, EP Patent Application No. 15819480.3, dated Feb. 16, 2018.
Biswas, P. "Immunomodulatory effects of bovine colostrum in human peripheral blood mononuclear cells" New Microbiologica, 30, 447-454, 2007.
International Search Report, International Patent Application No. PCT/US2015/039970, dated Jan. 12, 2016, 14 pages.
Konuspayeva et al. "Lactoferrin and imunoglobulin contents in camel's milk (*Camelus bactrainus, Camelus dromedarius*, and hybrids) from Kazakhstan" J. Dairy Sci. 2007, 90(1):38-46, Abstract, p. 39, col. 2; p. 45, col. 2.
Shin et al. "Use of Egg Yolk-Derived immunoglobulin as an Alternative to Antibiotic Treatment for Control of Helicobacter pylori Infection" Clin Diagn. Lab Immunol. 2002, 9(5):1061-1066.
Tsabouri et al. "Cow's milk Allergenicity" Endor Metab Immune Disord Drug Targets Mar. 2014, 14(1): 16-26.

* cited by examiner

*Primary Examiner* — G Steven Vanni
(74) *Attorney, Agent, or Firm* — Casimir Jones S.C.; J. Mitchell Jones

(57) ABSTRACT

The present invention provides a means to prepare a product from domestic animal milk, blood or eggs which comprises an array of T-cell exposed motifs similar in identity, distribution and concentration to those found in human immunoglobulin variable regions and to prepare and apply the product as an immune modulating agent for administration either as a nutritional supplement or as a pharmaceutical product.

18 Claims, 7 Drawing Sheets

FIG. 1

Figure 2:
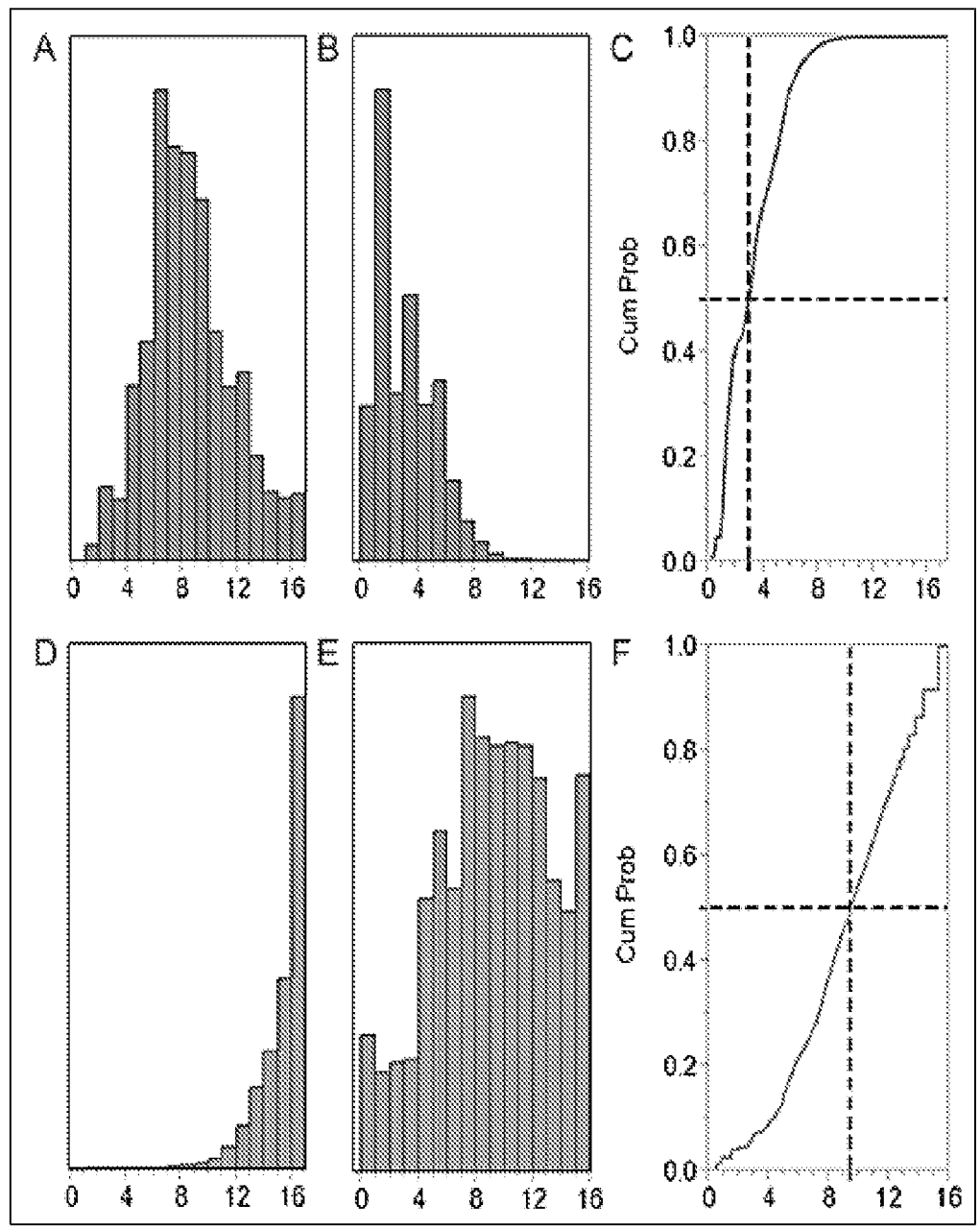

| Amino acid | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Pocket position | -3 | -2 | -1 | 1 | 2 | 3 | 4 | 5 | 6 | 7 | 8 | 9 | +1 | +2 | +3 |
| TCEM IIa |  |  |  |  | 2 | 3 |  | 5 |  | 7 | 8 |  |  |  |  |
| TCEM IIb |  |  | -1 |  |  | 3 |  | 5 |  | 7 | 8 |  |  |  |  |
| GEM IIa | -3 | -2 | -1 | 1 |  |  | 4 |  | 6 |  |  | 9 | +1 | +2 | +3 |
| GEM IIb | -3 | -2 |  | 1 | 2 |  | 4 |  | 6 |  |  | 9 | +1 | +2 | +3 |
| Pocket position | 1 | 2 | 3 | 4 | 5 | 6 | 7 | 8 | 9 |  |  |  |  |  |  |
| TCEM I |  |  |  | 4 | 5 | 6 | 7 | 8 |  |  |  |  |  |  |  |
| GEM I | 1 | 2 | 3 |  |  |  |  |  | 9 |  |  |  |  |  |  |

IMMUNOGLOBULIN POLYPEPTIDE FRACTIONS FROM PRODUCTS OF DOMESTIC ANIMALS

BACKGROUND OF THE INVENTION

The adaptive immune system is comprised of antibodies, generated by B-cells, and cell mediated immunity which depends on the recognition by T-cells of peptides bound in the major histocompatibility molecules and presented on the surface of antigen presenting cells (APCs) as a complex with major histocompatibility molecules (MHC). Many cell types may serve as APCs, but primarily they comprise dendritic cells, macrophages, and B-cells (the so called "professional" APCs). The presentation of peptides bound in MHC molecules is a function of cleavage of polypeptides by various endosomal peptidases, including but not limited to cathepsins, and the competitive binding of peptides to genetically defined MHC molecules.

The primary function of the adaptive immune system is to differentiate self from not-self and to allow the body to mount an appropriate response to molecules, once identified as self or as not-self. When a familiar self-antigen is recognized, the desired outcome is down-regulation of the immune response or tolerance. When an unfamiliar non-self antigen is encountered, the appropriate outcome is usually a robust up-regulation to yield an immune response in which cytokine responses enlist additional cellular responses to remove the foreign stimulus and protect the integrity of the host.

The discrimination between self and not-self is largely dependent on the T-cell responses and is the combination of the host's genetically determined MHC molecules in combination with motifs comprised in peptides which are bound by MHC molecules and exposed to T-cells in the context of the MHC molecules. Immunoglobulin variable regions provide a vast diversity of amino acid motifs recognized by T cells when presented as a component of a peptide-MHC complex. This occurs endogenously through the processing of an individual's own antibodies but is also achieved through the administration of exogenous immunoglobulins.

The provision of a balanced and diverse array of T-cell stimulating peptides, based on the amino acid motifs exposed to T cell receptors by peptides bound on MHC molecules, can therefore assist in maintaining an active and balanced immune response and in overcoming the dysregulation of the immune response in various autoimmune diseases and immunosuppression. Such an array of T-cell stimulating peptide motifs may be provided by a preparation of immunoglobulins, and in particular the immunoglobulin variable regions, derived from the milk, blood or eggs of domestic animals. Such administration may be achieved orally as a nutritional supplement or as a pharmaceutical preparation.

SUMMARY OF THE INVENTION

The present invention provides a means to prepare a product from domestic animal milk, blood or eggs which comprises an array of T-cell exposed motifs similar in identity, distribution and concentration to those found in human immunoglobulin variable regions and to prepare and apply the product as an immune modulating agent for administration either as a nutritional supplement or as a pharmaceutical product.

In one embodiment the protein product is derived by harvesting immunoglobulin containing milk, blood, or eggs from a domestic animal and comparing the distribution frequency of T cell exposed motifs in the harvested product to a reference database of TCEMs in human variable chain regions of germline origin, or somatically hypermutated origin or TCEMs found in the human immunoglobulin constant region to determine the degree of identity, comparability of the frequency distribution or concentration of TCEMs. In particular embodiments the domestic animal from which the immunoglobulins are harvested include the cow, sheep, buffalo, camel, swine, poultry, horse or rabbit. However, such examples are not limiting and immunoglobulins may be harvested from any animal kept for the purpose of harvesting products it produces.

In a particularly preferred embodiment the immunoglobulin containing product that is harvested is milk, which may include colostrum or milk produced throughout the duration of lactation. In yet other embodiments the immunoglobulins may be harvested from blood, either as a terminal event during slaughter, or on an ongoing basis from live animals. In instances where collection of immunoglobulins is from milk, the milk may be processed by separation of whey, including through the production of cheese to remove the casein content or by fermentation to make yoghurt and the concentration of milk solids to release the whey fraction, or by filtration. Milk collected for the purpose of utilization of the immunoglobulins may be processed by pasteurization or filtration.

In some particular embodiments the immunoglobulins may be partially cleaved by proteases to form smaller sub-chains. Such cleavages may be achieved by addition of enzymes or by the proteases expressed by bacteria during a fermentation process. Said bacteria may include genera typically used in the production of yogurt, fermented milk products, or cheese.

In one preferred embodiment the immunoglobulin containing product, which carries a characterized profile of TCEMS and/or concentration of TCEMs similar to that in human immunoglobulin, may be administered as a nutritional supplement. This may be a standalone supplement or in some particularly preferred embodiments this is achieved by addition of the TCEM enriched product back to another milk product such as yoghurt. In yet another preferred embodiment the TCEM characterized product may be administered as a pharmaceutical product in which case administration may be oral or parenteral.

The present invention further provides methods for the preparation of products from domestic animal immunoglobulins. In preferred embodiments the invention provides a means to characterize the T-cell exposed motifs in sequences extracted from the domestic animal immunoglobulins, identifying the TCEMs by application of a computer implemented algorithm and comparing these with reference databases previously established. Said reference databases document the frequency distribution of TCEMs in human germline immunoglobulin sequences found in variable regions, in human somatically hypermutated variable regions, and in human immunoglobulin constant regions. Such frequency distribution identifies which TCEMs occur in 1 in 2 variable regions, 1 in 4 variable regions and so on, based on a log based two classification up to a frequency of 1 in 64,000 variable regions.

In preferred applications of the method, the comparison of TCEMs in the domestic animal immunoglobulin composition identifies that at least 60% or 70% or 80% of TCEMs are the same as those found in a reference database of human germline or somatically mutated variable regions or in human constant regions. This enables the design of a product derived from domestic animal immunoglobulins which has a desired degree of overlap of TCEMs with human immunoglobulins. In yet other embodiments the composition of the immunoglobulin product is adjusted to achieve a desired concentration and frequency distribution of TCEMs that is similar to that in the reference databases.

In some embodiments the subject to whom the product is administered is a human however the product may also be administered to an animal and in particular may be administered to a companion animal.

In some embodiments the immunoglobulins harvested from domestic animals may be modified to increase the content of immunoglobulin variable regions relative to constant regions. In some instances this may be achieved by enzymatic digestion including digestion by pepsin. In yet other instances enzymatic digestion is achieved by exposure to proteases expressed by food fermentation bacteria including but not limited to *Lactobacuillus* spp, *Streptococcus* spp, and *Bifidobacterium* spp.

In further embodiments a formulation is prepared containing a known concentration of domestic animal immunoglobulin and the peptide and polypeptide derivatives thereof and prepared for oral delivery. In preferred embodiments said oral delivery is in the form of a capsule or tablet. In yet other formulations said delivery is as a liquid suspension or solution or as or powder or granules. Such formulations may be incorporated into enriched dairy products of milk or fermented milk or may be incorporated in to a gel or gum based product to make the dosage a chewable form. The oral formulation may, in one embodiment be delivered as a drink or beverage, while in other embodiments it is delivered as a functional food. In some preferred embodiments the oral delivery is to a young child or baby while in other embodiments the formulation is suitable for an adult and in particular, for the elderly.

In particular embodiments the oral administration of domestic animal immunoglobulin fractions of known concentration may also contain shorter peptide and polypeptide chains derived from immunoglobulins. The immunoglobulin polypeptide fraction may be mixed with probiotic bacteria.

A particularly desirable use of the oral formulation of domestic animal immunoglobulins of known concentration is in enhancing the immune response of a subject. In some embodiments the oral formulation may be administered in advance of vaccination in order to enhance the immune response. In yet other embodiments the oral formulation is administered to subjects with immune imbalances which have arisen as the result of autoimmune disease, infections, cancer, or therapy by transplantation or chemotherapy.

A further preferred embodiment is the use of oral formulation s of domestic animal immunoglobulins to assist in countering immune imbalances which can arise when other therapeutic drugs are being administered. This includes antibiotic administration which may disrupt the natural microbiome, especially the gastrointestinal microbiome. Another example is the administration of antibody based biotherapeutics which may disrupt the balance of the immune system and in particular when such biotherapeutic antibodies target components of the immune system such as, but not limited to, TNF alpha, CD20, CD33, CD52 and other targets.

Additional preferred applications are in the support of reestablishment of a balanced T cell population in individuals who have undergone transplant, immunosuppression, whether natural or iatrogenic, and patients who are recovering from cancer. Many other medical applications are possible and these examples are not considered limiting.

Preferably the embodiment of an oral formulation comprises a concentrated domestic animal immunoglobulin polypeptide fraction, such that said fraction comprises greater than about 75% w/w immunoglobulin polypeptides, wherein w/w is the weight of the immunoglobulin polypeptides per the total weight of the fraction on a dry basis, and said fraction further comprises a diversity of T-cell exposed amino acid motifs, which when taken up by antigen presenting cells of the consumer are bound by MHC molecules and bind to the T cells of the consumer, thus modulating the cellular immune response.

No special preparation of the donor animals is required; the immunoglobulin polypeptide fraction in the oral formulation may be prepared from bulk milk, plasma or eggs. Indeed it is desirable that the immunoglobulins are harvested from a wide diversity of individual donor animals and that no special preimmunization or hyperimmunization of said animals should have occurred.

FIGURES

FIG. 1: Positions of the amino acids in TCEM and GEM registers. Discontinuous sets of amino acids in peptides were placed into categorical groups based on the structural analysis of amino acid contact points in pMHC:T-cell receptor complexes (1). For MHC-II, T-cell exposed motifs are related to pocket positions in a 15-mer, with a conventional 9-mer core flanked by 3 amino acids on each end. A 9-mer is shown for MHC-I. Two types of class II T-cell exposed motifs, TCEM IIa and TCEM IIb are considered. They are discontinuous and occupy the register positions shown. TCEM IIa comprises amino acids 2,3,5,7,8 and TCEM IIb comprises −1,3,5,7,8. The obverse face of the 15-mer comprises the corresponding groove exposed motifs, GEM IIA and GEM IIb, which are primarily involved in peptide binding to the MHC. In approximately one-third of the MHC-II motifs, both unique TCEM IIa and TCEM IIb are present (i.e. effectively a discontinuous hexamer). The class I motif is a continuous series of amino acids occupying amino acid positions 4,5,6,7,8 in a conventional MHC-I pocket. The discontinuous GEM I, amino acids 1,2,3,9 are those amino acids primarily responsible for binding the peptide in the MHC-I.

FIG. 2: Frequency distributions of unique T-cell exposed motifs in IGHV3. Frequency distributions of unique TCEM IIa motifs found in 22,458 IGHV3-origin sequences, comprising a total of $2.2\times10^6$ possible motifs. Panels A-C show germline-origin motifs and Panels D-F show SHM-origin motifs. Panels A and D: histogram of frequency of occurrence (histogram bins as $-\log_2$). Panels Band E: frequency weighted histogram. Panels C and F: cumulative distribution frequency of B and E. The dashed lines depict the frequency distribution midpoint.

FIG. 3: Distribution of TCEM IIa found in the immunoglobulin heavy chain variable regions of all non-human species tested showing weighted distribution by human FC category. Left panel shows ranking against human germline TCEMs; right panel shows ranking against human somatically hypermutated sequences FIG. 4: Distribution of TCEM IIa found in the immunoglobulin heavy chain variable regions of bovine immunoglobulin tested showing weighted distribution by human FC category. Left panel shows ranking against human germline TCEMs; right panel shows ranking against human somatically hypermutated sequences. The large spikes in the SHM frequency pattern is due to the use of a relatively few TCEM patterns flanking CDR 3 that is found in every variable region. The bovine dataset only includes 221 difference sequences or only about 0.5% of the size of the human database is compared against. It is expected that the more rare motifs will increase in a larger database.

Figure 5:
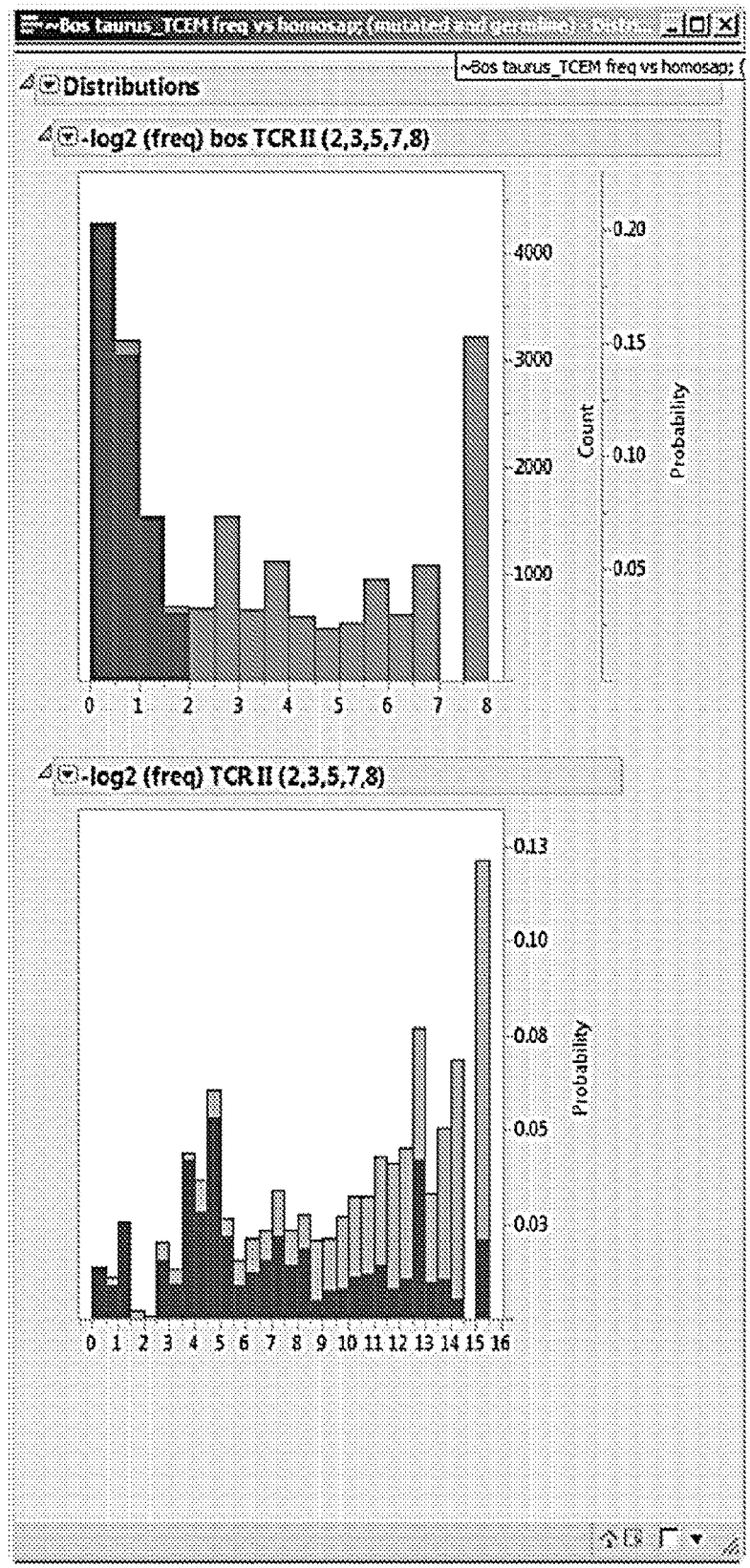

FIG. 5: Comparison of frequency class profile of human vs bovine. The top panel shows the frequency pattern of TCEM IIa motifs (i.e. 74% of the total motifs in bIGHV shown in Example 2) in the bovine dataset that are identical to those in hIGHV. The shaded area represents the motifs that are bovine germline origin (found in over 50%) of the individual sequences. The lower panel is the frequency pattern of the bIGHV TCEM IIa motifs in the 40K human database. The shaded area shows the region of the bovine germline motifs are found in the high frequency region of the hIGHV.

Figure 6A:
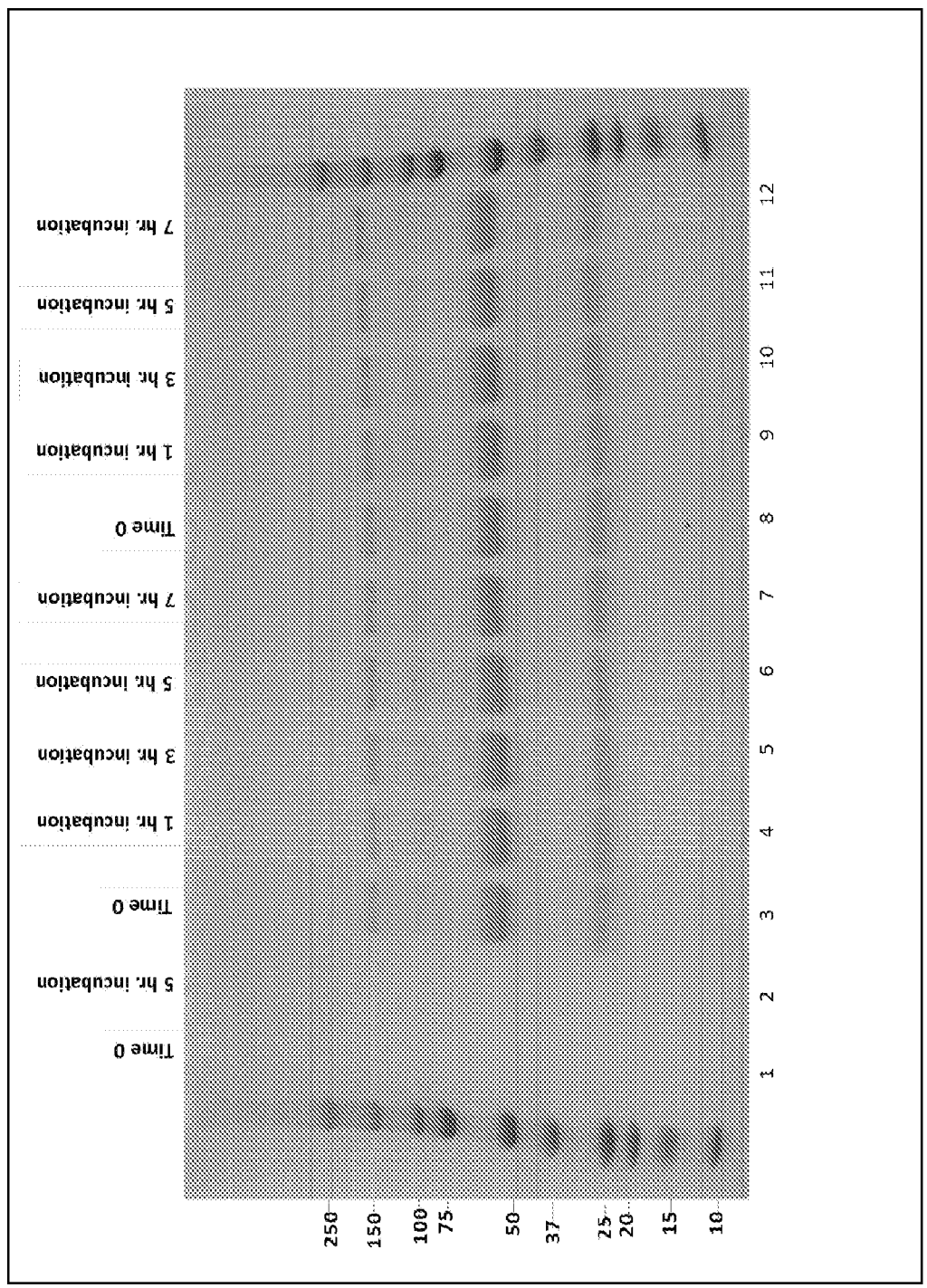
Figure 6B:
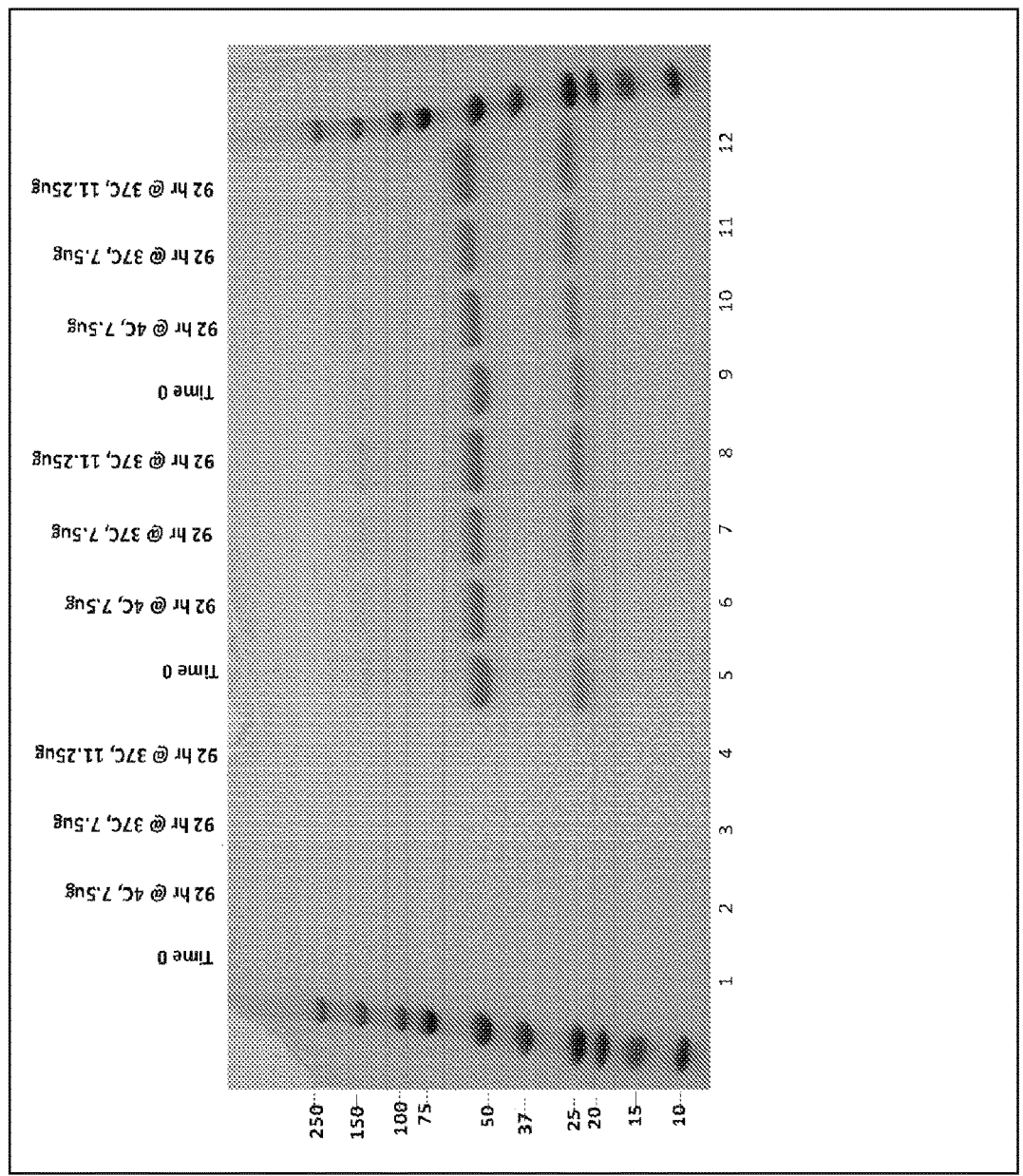

FIG. 6A-6B: Bovine immunoglobulins exposed to probiotic bacteria.

DEFINITIONS

As used herein, the term "genome" refers to the genetic material (e.g., chromosomes) of an organism or a host cell.

As used herein, the term "proteome" refers to the entire set of proteins expressed by a genome, cell, tissue or organism. A "partial proteome" refers to a subset the entire set of proteins expressed by a genome, cell, tissue or organism. Examples of "partial proteomes" include, but are not limited to, transmembrane proteins, secreted proteins, and proteins with a membrane motif. Human proteome refers to all the proteins comprised in a human being. Multiple such sets of proteins have been sequenced and are accessible at the InterPro international repository (www.e-bi.ac.uk/interpro). Human proteome is also understood to include those proteins and antigens thereof which may be over-expressed in certain pathologies, or expressed in a different isoforms in certain pathologies. Hence, as used herein, tumor associated antigens are considered part of the human proteome.

As used herein, the terms "protein," "polypeptide," and "peptide" refer to a molecule comprising amino acids joined via peptide bonds. In general "peptide" is used to refer to a sequence of 20 or less amino acids and "polypeptide" is used to refer to a sequence of greater than 20 amino acids.

As used herein, the term, "synthetic polypeptide," "synthetic peptide" and "synthetic protein" refer to peptides, polypeptides, and proteins that are produced by a recombinant process (i.e., expression of exogenous nucleic acid encoding the peptide, polypeptide or protein in an organism, host cell, or cell-free system) or by chemical synthesis.

As used herein, the term "protein of interest" refers to a protein encoded by a nucleic acid of interest. It may be applied to any protein to which further analysis is applied or the properties of which are tested or examined. Similarly, as used herein, "target protein" may be used to describe a protein of interest that is subject to further analysis.

As used herein "peptidase" refers to an enzyme which cleaves a protein or peptide. The term peptidase may be used interchangeably with protease, proteinases, oligopeptidases, and proteolytic enzymes. Peptidases may be endopeptidases (endoproteases), or exopeptidases (exoproteases). Similarly the term peptidase inhibitor may be used interchangeably with protease inhibitor or inhibitor of any of the other alternate terms for peptidase.

As used herein, the term "exopeptidase" refers to a peptidase that requires a free N-terminal amino group, C-terminal carboxyl group or both, and hydrolyses a bond not more than three residues from the terminus. The exopeptidases are further divided into aminopeptidases, carboxypeptidases, dipeptidyl-peptidases, peptidyl-dipeptidases, tripeptidyl-peptidases and dipeptidases.

As used herein, the term "endopeptidase" refers to a peptidase that hydrolyses internal, alpha-peptide bonds in a polypeptide chain, tending to act away from the N-terminus or C-terminus. Examples of endopeptidases are chymotrypsin, pepsin, papain and cathepsins. A very few endopeptidases act a fixed distance from one terminus of the substrate, an example being mitochondrial intermediate peptidase. Some endopeptidases act only on substrates smaller than proteins, and these are termed oligopeptidases. An example of an oligopeptidase is thimet oligopeptidase. Endopeptidases initiate the digestion of food proteins, generating new N- and C-termini that are substrates for the exopeptidases that complete the process. Endopeptidases also process proteins by limited proteolysis. Examples are the removal of signal peptides from secreted proteins (e.g. signal peptidase I,) and the maturation of precursor proteins (e.g. enteropeptidase, furin). In the nomenclature of the Nomenclature Committee of the International Union of Biochemistry and Molecular Biology (NC-IUBMB) endopeptidases are allocated to sub-subclasses EC 3.4.21, EC 3.4.22, EC 3.4.23, EC 3.4.24 and EC 3.4.25 for serine-, cysteine-, aspartic-, metallo- and threonine-type endopeptidases, respectively. Endopeptidases of particular interest are the cathepsins, and especially cathepsin B, L and S known to be active in antigen presenting cells.

As used herein, the term "immunogen" refers to a molecule which stimulates a response from the adaptive immune system, which may include responses drawn from the group comprising an antibody response, a cytotoxic T cell response, a T helper response, and a T cell memory. An immunogen may stimulate an upregulation of the immune response with a resultant inflammatory response, or may result in down regulation or immunosuppression. Thus the T-cell response may be a T regulatory response.

As used herein, the term "native" (or wild type) when used in reference to a protein refers to proteins encoded by the genome of a cell, tissue, or organism, other than one manipulated to produce synthetic proteins.

As used herein, the term "B-cell epitope" refers to a polypeptide sequence that is recognized and bound by a B-cell receptor. A B-cell epitope may be a linear peptide or may comprise several discontinuous sequences which together are folded to form a structural epitope. Such component sequences which together make up a B-cell epitope are referred to herein as B-cell epitope sequences. Hence, a B-cell epitope may comprise one or more B-cell epitope sequences. Hence, a B cell epitope may comprise one or more B-cell epitope sequences. A linear B-cell epitope may comprise as few as 2-4 amino acids or more amino acids.

As used herein, the term "predicted B-cell epitope" refers to a polypeptide sequence that is predicted to bind to a B-cell receptor by a computer program, for example, as described in PCT US2011/029192, PCT US2012/055038, and US2014/014523, each of which is incorporated herein by reference, and in addition by Bepipred (Larsen, et al., Immunome Research 2:2, 2006.) and others as referenced by Larsen et al (ibid) (Hopp T et al PNAS 78:3824-3828, 1981; Parker J et al, Biochem. 25:5425-5432, 1986). A predicted B-cell epitope may refer to the identification of B-cell epitope sequences forming part of a structural B-cell epitope or to a complete B-cell epitope.

As used herein, the term "T-cell epitope" refers to a polypeptide sequence which when bound to a major histocompatibility protein molecule provides a configuration recognized by a T-cell receptor. Typically, T-cell epitopes are presented bound to a MHC molecule on the surface of an antigen-presenting cell.

As used herein, the term "predicted T-cell epitope" refers to a polypeptide sequence that is predicted to bind to a major histocompatibility protein molecule by the neural network algorithms described herein, by other computerized methods, or as determined experimentally.

As used herein, the term "major histocompatibility complex (MHC)" refers to the MHC Class I and MHC Class II genes and the proteins encoded thereby. Molecules of the MHC bind small peptides and present them on the surface of cells for recognition by T-cell receptor-bearing T-cells. The MHC-Is both polygenic (there are several MHC class I and MHC class II genes) and polyallelic or polymorphic (there are multiple alleles of each gene). The terms MHC-I, MHC-II, MHC-1 and MHC-2 are variously used herein to indicate these classes of molecules. Included are both classical and nonclassical MHC molecules. An MHC molecule is made up of multiple chains (alpha and beta chains) which associate to form a molecule. The MHC molecule contains a cleft or groove which forms a binding site for peptides. Peptides bound in the cleft or groove may then be presented to T-cell receptors. The term "MHC binding region" refers to the groove region of the MHC molecule where peptide binding occurs.

As used herein, the term "haplotype" refers to the HLA alleles found on one chromosome and the proteins encoded thereby. Haplotype may also refer to the allele present at any one locus within the MHC. Each class of MHC-Is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein. HLA alleles are listed at hla.alleles.org/nomenclature/naming.html, which is incorporated herein by reference.

The MHCs exhibit extreme polymorphism: within the human population there are, at each genetic locus, a great number of haplotypes comprising distinct alleles—the IMGT/HLA database release (February 2010) lists 948 class I and 633 class II molecules, many of which are represented at high frequency (>1%). MHC alleles may differ by as many as 30-aa substitutions. Different polymorphic MHC alleles, of both class I and class II, have different peptide specificities: each allele encodes proteins that bind peptides exhibiting particular sequence patterns.

The naming of new HLA genes and allele sequences and their quality control is the responsibility of the WHO Nomenclature Committee for Factors of the HLA System, which first met in 1968, and laid down the criteria for successive meetings. This committee meets regularly to discuss issues of nomenclature and has published 19 major reports documenting firstly the HLA antigens and more recently the genes and alleles. The standardization of HLA antigenic specifications has been controlled by the exchange of typing reagents and cells in the International Histocompatibility Workshops. The IMGT/HLA Database collects both new and confirmatory sequences, which are then expertly analyzed and curated before been named by the Nomenclature Committee. The resulting sequences are then included in the tools and files made available from both the IMGT/HLA Database and at hla.alleles.org.

Each HLA allele name has a unique number corresponding to up to four sets of digits separated by colons. See e.g., hla.alleles.org/nomenclature/naming.html which provides a description of standard HLA nomenclature and Marsh et al., Nomenclature for Factors of the HLA System, 2010 Tissue Antigens 2010 75:291-455. HLA-DRB1*13:01 and HLA-DRB1*13:01:01:02 are examples of standard HLA nomenclature. The length of the allele designation is dependent on the sequence of the allele and that of its nearest relative. All alleles receive at least a four digit name, which corresponds to the first two sets of digits, longer names are only assigned when necessary.

The digits before the first colon describe the type, which often corresponds to the serological antigen carried by an allotype, The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns or in the 5' or 3' untranslated regions that flank the exons and introns are distinguished by the use of the fourth set of digits. In addition to the unique allele number there are additional optional suffixes that may be added to an allele to indicate its expression status. Alleles that have been shown not to be expressed, 'Null' alleles have been given the suffix 'N'. Those alleles which have been shown to be alternatively expressed may have the suffix 'L', 'S', 'C', 'A' or 'Q'. The suffix 'L' is used to indicate an allele which has been shown to have 'Low' cell surface expression when compared to normal levels. The 'S' suffix is used to denote an allele specifying a protein which is expressed as a soluble 'Secreted' molecule but is not present on the cell surface. A 'C' suffix to indicate an allele product which is present in the 'Cytoplasm' but not on the cell surface. An 'A' suffix to indicate 'Aberrant' expression where there is some doubt as to whether a protein is expressed. A 'Q' suffix when the expression of an allele is 'Questionable' given that the mutation seen in the allele has previously been shown to affect normal expression levels.

In some instances, the HLA designations used herein may differ from the standard HLA nomenclature just described due to limitations in entering characters in the databases described herein. As an example, DRB1_0104, DRB1*0104, and DRB1-0104 are equivalent to the standard nomenclature of DRB1*01:04. In most instances, the asterisk is replaced with an underscore or dash and the semicolon between the two digit sets is omitted.

As used herein, the term "polypeptide sequence that binds to at least one major histocompatibility complex (MHC) binding region" refers to a polypeptide sequence that is recognized and bound by one more particular MHC binding regions as predicted by the neural network algorithms described herein or as determined experimentally.

As used herein the terms "canonical" and "non-canonical" are used to refer to the orientation of an amino acid sequence. Canonical refers to an amino acid sequence presented or read in the N terminal to C terminal order; non-canonical is used to describe an amino acid sequence presented in the inverted or C terminal to N terminal order.

As used herein, the term "allergen" refers to an antigenic substance capable of producing immediate hypersensitivity and includes both synthetic as well as natural immunostimulant peptides and proteins. Allergen includes but is not limited to any protein or peptide catalogued in the Structural Database of Allergenic Proteins database http://fermi.utmb.edu/SDAP/index.html As used herein, the term "consensus protease cleavage site" refers to an amino acid sequence that is recognized by a protease such as trypsin or pepsin.

As used herein, the term "affinity" refers to a measure of the strength of binding between two members of a binding pair, for example, an antibody and an epitope and an epitope and a MHC-I or II haplotype. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT\ LN(K)$ where R=gas constant and temperature is in degrees Kelvin. Affinity may be determined experimentally, for example by surface plasmon resonance (SPR) using commercially available Biacore SPR units (GE Healthcare) or in silico by methods such as those described herein in detail. Affinity may also be expressed as the ic50 or inhibitory concentration 50, that concentration at which 50% of the peptide is displaced. Likewise ln(ic50) refers to the natural log of the ic50.

The term "$K_{off}$", as used herein, is intended to refer to the off rate constant, for example, for dissociation of an antibody from the antibody/antigen complex, or for dissociation of an epitope from an MHC haplotype.

The term "$K_d$", as used herein, is intended to refer to the dissociation constant (the reciprocal of the affinity constant "Ka"), for example, for a particular antibody-antigen interaction or interaction between an epitope and an MHC haplotype.

As used herein, the terms "strong binder" and "strong binding" and "High binder" and "high binding" or "high affinity" refer to a binding pair or describe a binding pair that have an affinity of greater than $2 \times 10^7 M^{-1}$ (equivalent to a dissociation constant of 50 nM Kd)

As used herein, the term "moderate binder" and "moderate binding" and "moderate affinity" refer to a binding pair or describe a binding pair that have an affinity of from $2 \times 10^7 M^{-1}$ to $2 \times 10^6 M^{-1}$.

As used herein, the terms "weak binder" and "weak binding" and "low affinity" refer to a binding pair or describe a binding pair that have an affinity of less than $2 \times 10^6 M^{-1}$ (equivalent to a dissociation constant of 500 nM Kd)

Binding affinity may also be expressed by the standard deviation from the mean binding found in the peptides making up a protein. Hence a binding affinity may be expressed as "$-1\sigma$" or "$<-1\sigma$", where this refers to a binding affinity of 1 or more standard deviations below the mean. A common mathematical transformation used in statistical analysis is a process called standardization wherein the distribution is transformed from its standard units to standard deviation units where the distribution has a mean of zero and a variance (and standard deviation) of 1. Because each protein comprises unique distributions for the different MHC alleles standardization of the affinity data to zero mean and unit variance provides a numerical scale where different alleles and different proteins can be compared. Analysis of a wide range of experimental results suggest that a criteria of standard deviation units can be used to discriminate between potential immunological responses and non-responses. An affinity of 1 standard deviation below the mean was found to be a useful threshold in this regard and thus approximately 15% (16.2% to be exact) of the peptides found in any protein will fall into this category.

The terms "specific binding" or "specifically binding" when used in reference to the interaction of an antibody and a protein or peptide or an epitope and an MHC haplotype means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein "immunoglobulin" means the distinct antibody molecule secreted by a clonal line of B cells; hence when the term "100 immunoglobulins" is used it conveys the distinct products of 100 different B-cell clones and their lineages.

An "immunoglobulin polypeptide fraction" as used herein refers to a composition comprising whole immunoglobulins and derivative peptides and polypeptides thereof from 10 amino acids to 250 amino acids in length.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "support vector machine" refers to a set of related supervised learning methods used for classification and regression. Given a set of training examples, each marked as belonging to one of two categories, an SVM training algorithm builds a model that predicts whether a new example falls into one category or the other.

As used herein, the term "classifier" when used in relation to statistical processes refers to processes such as neural nets and support vector machines.

As used herein "neural net", which is used interchangeably with "neural network" and sometimes abbreviated as NN, refers to various configurations of classifiers used in machine learning, including multilayered perceptrons with one or more hidden layer, support vector machines and dynamic Bayesian networks. These methods share in common the ability to be trained, the quality of their training evaluated and their ability to make either categorical classifications or of continuous numbers in a regression mode. Perceptron as used herein is a classifier which maps its input x to an output value which is a function of x, or a graphical representation thereof.

As used herein, the term "principal component analysis", or as abbreviated PCA, refers to a mathematical process which reduces the dimensionality of a set of data (Wold, S., Sjorstrom, M., and Eriksson, L., Chemometrics and Intelligent Laboratory Systems 2001. 58: 109-130; Multivariate and Megavariate Data Analysis Basic Principles and Applications (Parts I&II) by L. Eriksson, E. Johansson, N. Kettaneh-Wold, and J. Trygg, 2006 $2^{nd}$ Edit. Umetrics Academy). Derivation of principal components is a linear transformation that locates directions of maximum variance in the original input data, and rotates the data along these axes. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Further, the principal components are scale-independent in that they can be developed from different types of measurements. A description of the application of PCA to generate descriptors or amino acids and by combination thereof peptides is provided in PCT US2011/029192 incorporated herein by reference As used herein, the term "vector" when used in relation to a computer algorithm or the present invention, refers to the mathematical properties of the amino acid sequence.

As used herein, the term "vector," when used in relation to recombinant DNA technology, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

As used herein, the terms "biocide" or "biocides" refer to at least a portion of a naturally occurring or synthetic molecule (e.g., peptides or enzymes) that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the terms "protein biocide" and "protein biocides" refer to at least a portion of a naturally occurring or synthetic peptide molecule or enzyme that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the term "neutralization," "pathogen neutralization," refer to destruction or inactivation (e.g., loss of virulence) of a "pathogen" (e.g., bacterium, parasite, virus, fungus, mold, prion, and the like) thus preventing the pathogen's ability to initiate a disease state in a subject.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "subject" is an animal such as vertebrate, preferably a mammal such as a human, a bird, or a fish. Mammals are understood to include, but are not limited to, murines, simians, humans, bovines, cervids, equines, porcines, canines, felines etc.).

An "effective amount" is an amount sufficient to effect beneficial or desired results. An effective amount can be administered in one or more administrations, As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The terms "bacteria" and "bacterium" refer to prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause product degradation or spoilage. "Food fermentation bacteria" are bacteria used in the preparation of fermented products and include but are not limited to *Lactobacillus* spp, *Streptococcus* spp and *Bifidobacterium* spp.

"Strain" as used herein in reference to a microorganism describes an isolate of a microorganism (e.g., bacteria, virus, fungus, parasite) considered to be of the same species but with a unique genome and, if nucleotide changes are non-synonymous, a unique proteome differing from other strains of the same organism. Typically strains may be the result of isolation from a different host or at a different location and time but multiple strains of the same organism may be isolated from the same host.

As used herein "Complementarity Determining Regions" (CDRs) are those parts of the immunoglobulin variable chains which determine how these molecules bind to their specific antigen. Each immunoglobulin variable region typically comprises three CDRs and these are the most highly variable regions of the molecule.

As used herein, the term "motif" refers to a characteristic sequence of amino acids forming a distinctive pattern.

The term "Groove Exposed Motif" (GEM) as used herein refers to a subset of amino acids within a peptide that binds to an MHC molecule; the GEM comprises those amino acids which are turned inward towards the groove formed by the MHC molecule and which play a significant role in determining the binding affinity. In the case of human MHC-I the GEM amino acids are typically (1,2,3,9). In the case of MHC-II molecules two formats of GEM are most common comprising amino acids (−3,2,−1,1,4,6,9,+1,+2,+3) and (−3, 2,1,2,4,6,9,+1,+2,+3) based on a 15-mer peptide with a central core of 9 amino acids numbered 1-9 and positions outside the core numbered as negative (N terminal) or positive (C terminal).

"Immunoglobulin germline" is used herein to refer to the variable region sequences encoded in the inherited germline genes and which have not yet undergone any somatic hypermutation. Each individual carries and expresses multiple copies of germline genes for the variable regions of heavy and light chains. These undergo somatic hypermutation during affinity maturation. Information on the germline sequences of immunoglobulins is collated and referenced by www.imgt.org (2). "Germline family" as used herein refers to the 7 main gene groups, catalogued at IMGT, which share similarity in their sequences and which are further subdivided into subfamilies.

"Affinity maturation" is the molecular evolution that occurs during somatic hypermutation during which unique variable region sequences generated that are the best at targeting and neutralizing and antigen become clonally expanded and dominate the responding cell populations.

"Germline motif" as used herein describes the amino acid subsets that are found in germline immunoglobulins. Germline motifs comprise both GEM and TCEM motifs found in the variable regions of immunoglobulins which have not yet undergone somatic hypermutation.

"Immunopathology" when used herein describes an abnormality of the immune system. An immunopathology may affect B-cells and their lineage causing qualitative or quantitative changes in the production of immunoglobulins. Immunopathologies may alternatively affect T-cells and result in abnormal T-cell responses. Immunopathologies may also affect the antigen presenting cells. Immunopathologies may be the result of neoplasias of the cells of the immune system. Immunopathology is also used to describe diseases mediated by the immune system such as autoimmune diseases. Illustrative examples of immunopathologies include, but are not limited to, B-cell lymphoma, T-cell lymphomas, Systemic Lupus Erythematosus (SLE), allergies, hypersensitivities, immunodeficiency syndromes, radiation exposure or chronic fatigue syndrome.

"Autoimmune disease" as used herein refers to a disease in which the immune response is directed against self epitopes. Autoimmune diseases include an array of dysregulations or imbalances of self-recognition. Adverse immune responses may arise through up-regulation (for instance when an infectious agent provides an epitope mimic) or conversely by loss of self-tolerance. Among the diseases recognized to be the result of autoimmunity, or to have an autoimmune component, are celiac disease, narcolepsy, rheumatoid arthritis and multiple sclerosis (Jones, E. Y. et al, 2006. Nat. Rev. Immunol. 6:271-282.). Other autoimmune diseases include but are not limited to Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Celiac disease, Cogan syndrome, Cold agglutinin disease, Crohn's Disease, Dermatomyositis, Diabetes mellitus type 1, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Pemphigus vulgaris, Polymyositis, Primary biliary cirrhosis, Psoriasis, Psoriatic Arthritis, Relapsing polychondritis, Rheumatoid arthritis, Sjögren's syndrome, Temporal arteritis, Ulcerative Colitis, Vasculitis, and Wegener's granulomatosis. In a number of other instances microbial infections are known to lead to a subsequent autoimmune reaction, including, for example but not limited to, in Lyme Disease, Streptococcal infections, and chronic respiratory infections (Hildenbrand, P. et al, 2009. Am. J. Neuroradiol. 30:1079-1087; Lee, J. L. et al, Autoimmun. Rev. 10.1016 0.2009; Leidinger, P. et al Respir. Res. 10:20, 2009), Guillan Barre (Yuki N (2001) *Lancet Infect Dis* 1 (1): 29-37, Yuki N (2005) *Curr Opin Immunol* 17 (6): 577-582; Kieseier B C et al, (2004) *Muscle Nerve* 30 (2): 131-156), rheumatoid arthritis (Rashid T et al (2007) *Clin Exp Rheumatol* 25 (2): 259-267), rheumatic fever (Guilherme L, Kalil J (2009) *J Clin Immunol*), narcolepsy (de la Herrera Arita 2013[7].

"Immune dysregulation" as used herein described any imbalance in the immune response whether or not that imbalance rises to the level of causing a clinical autoimmune disease or immunopathology.

As used herein "modulating the immune response" or "immune modulation" refers to a change in the numbers of T regulatory cells, a change in the numbers or ratio of CD8 and CD4 T lymphocytes, or a change in the cytokine profile in any tissue.

As used herein "immune imbalance" refers to an abnormally high or low ratio of T-regulatory cells to T effector cells in any selected tissue.

"Obverse" as used herein describes the outward directed face or the side facing outwards. Hence, in the context of a pMHC complex, the obverse side is that face presented to the T-cell receptor and comprises the space-shape made up of the TCEM and the contiguous and surrounding outward facing components of the MHC molecule that will be different for each different MHC allele.

"pMHC" Is used to describe a complex of a peptide bound to an MHC molecule. In many instances a peptide bound to an MHC-I will be a 9-mer or 10-mer however other sizes of 7-11 amino acids may be thus bound. Similarly MHC-II molecules may form pMHC complexes with peptides of 15 amino acids or with peptides of other sizes from 11-23 amino acids. The term pMHC is thus understood to include any short peptide bound to a corresponding MHC.

"Somatic hypermutation" (SHM), as used herein refers to the process by which variability in the immunoglobulin variable region is generated during the proliferation of individual B-cells responding to an immune stimulus. SHM occurs in the complementarity determining regions.

"T-cell exposed motif" (TCEM), as used herein, refers to the sub set of amino acids in a peptide bound in a MHC molecule which are directed outwards and exposed to a T-cell binding to the pMHC complex. A T-cell binds to a complex molecular space-shape made up of the outer surface MHC of the particular HLA allele and the exposed amino acids of the peptide bound within the MHC. Hence any T-cell recognizes a space shape or receptor which is specific to the combination of HLA and peptide. The amino acids which comprise the TCEM in an MHC-I binding peptide typically comprise positions 4, 5, 6, 7, 8 of a 9-mer. The amino acids which comprise the TCEM in an MHC-II binding peptide typically comprise 2, 3, 5, 7, 8 or −1, 3, 5, 7, 8 based on a 15-mer peptide with a central core of 9 amino acids numbered 1-9 and positions outside the core numbered as negative (N terminal) or positive (C terminal). As indicated under pMHC, the peptide bound to a MHC may be of other lengths and thus the numbering system here is considered a non-exclusive example of the instances of 9-mer and 15 mer peptides.

"Regulatory T-cell" or "Treg" as used herein, refers to a T-cell which has an immunosuppressive or down-regulatory function. Regulatory T-cells were formerly known as suppressor T-cells. Regulatory T-cells come in many forms but typically are characterized by expression CD4+, CD25, and Foxp3. Tregs are involved in shutting down immune responses after they have successfully eliminated invading organisms, and also in preventing immune responses to self-antigens or autoimmunity.

"Tregitope" as used herein describes an epitope to which a Treg or regulatory T-cell binds.

"uTOPET™ analysis" as used herein refers to the computer assisted processes for predicting binding of peptides to MHC and predicting cathepsin cleavage, described in PCT US2011/029192, PCT US2012/055038, and US2014/01452, each of which is incorporated herein by reference.

"Framework region" as used herein refers to the amino acid sequences within an immunoglobulin variable region which do not undergo somatic hypermutation.

"Isotype" as used herein refers to the related proteins of particular gene family. Immunoglobulin isotype refers to the distinct forms of heavy and light chains in the immunoglobulins. In heavy chains there are five heavy chain isotypes (alpha, delta, gamma, epsilon, and mu, leading to the formation of IgA, IgD, IgG, IgE and IgM respectively) and light chains have two isotypes (kappa and lambda). Isotype when applied to immunoglobulins herein is used interchangeably with immunoglobulin "class".

"Class switch recombination" (CSR) as used herein refers to the change from one isotype of immunoglobulin to another in an activated B cell, wherein the constant region associated with a specific variable region is changed, typically from IgM to IgG or other isotypes.

"Immunostimulation" as used herein refers to the signaling that leads to activation of an immune response, whether said immune response is characterized by a recruitment of cells or the release of cytokines which lead to suppression of the immune response. Thus immunostimulation refers to both upregulation or down regulation.

Upregulation as used herein refers to an immunostimulation which leads to cytokine release and cell recruitment tending to eliminate a non self or exogenous epitope. Such responses include recruitment of T cells, including effectors such as cytotoxic T cells, and inflammation. In an adverse reaction upregulation may be directed to a self-epitope.

Down regulation as used herein refers to an immunostimulation which leads to cytokine release that tends to dampen or eliminate a cell response. In some instances such elimination may include apoptosis of the responding T cells.

"Frequency class" or "frequency classification" as used herein is used to describe the counts of TCEM motifs found in a given dataset of peptides. A logarithmic (log base 2) frequency categorization scheme was developed to describe the distribution of motifs in a dataset. As the cellular interactions between T-cells and antigen presenting cells displaying the motifs in MHC molecules on their surfaces are the ultimate result of the molecular interactions, using a log base 2 system implies that each adjacent frequency class would double or halve the cellular interactions with that motif. Thus using such a frequency categorization scheme makes it possible to characterize subtle differences in motif usage as well as providing a comprehensible way of visualizing the cellular interaction dynamics with the different motifs. Hence a Frequency Class 2, or FC 2 means 1 in 4, a Frequency class 10 or FC 10 means 1 in $2^{10}$ or 1 in 1024.

"40K set" as used herein refers to the database of 40,000 IGHV assembled from Genbank as described in Example 1

IGHV as used herein is an abbreviation for immunoglobulin heavy chain variable regions IGLV as used herein is an abbreviation for immunoglobulin light chain variable regions "Adverse immune response" as used herein may refer to (a) the induction of immunosuppression when the appropriate response is an active immune response to eliminate a pathogen or tumor or (b) the induction of an upregulated active immune response to a self-antigen or (c) an excessive upregulation unbalanced by any suppression, as may occur for instance in an allergic response.

As used herein "epitope mimic" or "TCEM mimic" is used to describe a peptide which has an identical or overlapping TCEM, but may have a different GEM. Such a mimic occurring in one protein may induce an immune response directed towards another protein which carries the same TCEM motif. This may give rise to autoimmunity or inappropriate responses to the second protein.

"Domestic animal" as used herein refers to any species customarily maintained in domestication in any environment or ethnic culture including but not limited to cows, buffalo, camels, sheep, goats, horses, poultry, swine and llama. Although this invention refers in part to milk products, it also includes blood products and thus domestic animals as used herein extends to rabbits, chickens and other domestic fowl such as geese and ducks.

"Milk" as used herein is the normal lacteal secretion of the mammary gland of a mammal. Milk includes the secretions produced at any stage of lactation and thus includes colostrum produced in the first few days of lactation as well as milk of the remainder of lactation.

"Milk product" as used herein refers to whole milk or any derivative thereof. Thus it encompasses, but is not limited to, skim milk, nonfat milk, whey, filtered whey, acid whey, sweet whey, milk solids, fermented or cultured milk products, cream, buttermilk, cheese, yoghurt. "Fermented milk product" includes, but is not limited to, yogurt, kefir, kumis, lassi and other milk products fermented with fermentation bacteria.

"Blood product" as used herein refers to whole blood or any derivative thereof. Thus it encompasses, but is not limited to, serum, plasma, clotted blood, dried blood.

"Companion animal" as used herein refers to the species of animals kept as pets or for enjoyment, not for food production. Hence it includes, but is not limited to, dogs, cats, horses, and donkeys.

"Poultry" as used herein refers to any domesticated avian species including but not limited to chickens, ducks, geese, quail, and pheasants.

As used herein the term "harvested" is used to describe removal and collection of a product from its source. Hence the term is used to describe collection of products produced by domestic animals. This includes the collection of milk products by milking an animal, typically combining the milk products from multiple animals together, and processing of the milk by cooling, fractionating and other processing steps. Similarly harvesting may be used to describe blood collection, whether as a by-product of slaughter of a domestic animal for meat or by periodic venipuncture of a live animal and collection of blood. Harvesting may also refer to the collection and processing of eggs.

"Probiotic" as used herein comprises one or more a bacteria or yeast generally recognized as safe, which are thought to convey health benefits and may be included in a food product. Some food fermentation bacteria as defined above fall within the definition of probiotics.

"Livestock species" as used herein refers to those domestic animal species husbanded for the production of meat, milk, eggs or fiber. Such species include but are not limited to cattle, sheep, goats, pigs, poultry, camels, rabbits, mink and chinchilla.

"Infant formula" as used herein refers to compositions formulated for feeding to babies as a substitute or supplement for human breastmilk.

"Recombinant antibody based therapeutic" as used herein refers to any biopharmaceutical composition which comprises a monoclonal antibody component, whether said monoclonal is of human, humanized or murine origin. Examples, considered non limiting, include Rituximab®, Adalimumab®, Alemtuzumab®, or others, as listed for instance in Baker M, et al. Self Nonself. 2010 October-December; 1(4): 314-322.

DETAILED DESCRIPTION OF THE INVENTION

Any protein taken up by an antigen presenting cell (APC) can be processed to lead to stimulation of an immune response. Proteins may be derived from endogenous sources, such as cellular proteins and antibodies or from exogenous sources, including but not limited to pathogens, allergens and other environmental proteins. Antigen presenting cells include, but are not limited to, dendritic cells, B-cells and macrophages. Peptides may be presented on the surface of any cell bound to MHC molecules. Each cell carries MHC molecules encoded in various gene loci and heterozygous copies thereof. Each allele of each MHC locus has a unique binding groove which engages peptides released by enzyme action from proteins. The endopeptidase cleavage to release peptides and the binding reaction between short peptides and the MHC molecules has been well studied and modelled (see, e.g., PCT US2011/029192, PCT US2012/055038, US2014/014523, and PCT US2014/041525, each of which is incorporated herein by reference).

The present invention relates to the design of nutritional and pharmaceutical products based on an understanding of the interaction between a T-cell receptor and the complex of a peptide bound in a MHC molecular groove. The peptides which binding MHC grooves are typically a 9-mer binding an MHC-I and a 15-mer binding in a MHC-II groove. In a preferred embodiment therefore these peptide sizes are used throughout the analyses presented herein. However these peptide lengths should not be considered limiting and the same processes can be implemented and used as the basis for analysis of peptides of 7-11 amino acids in the case of MHC-I molecules and peptides of 11-23 amino acids for MHC-II alleles. Peptides which are bound in MHC grooves comprise two sets of amino acids: those that face inwards into the groove and determine the binding affinity to the MHC molecule (the groove exposed motifs or GEM) and those which do not interact with the groove, but rather are on the obverse side exposed outwardly to the T-cells (the T-cell exposed motifs or TCEM). In the case of MHC-I, molecules the central amino acids 4, 5, 6, 7, 8 of the typical nonamer peptide bound form the T-cell exposed motif or TCEM, while the binding affinity to the groove is determined by amino acids 1, 2, 3, 9, the groove exposed motif or GEM. It has been recognized that two sets of amino acid positions may form these configurations for MHC-II presentation (Rudolph et al How TCRs bind MHCs, peptides, and coreceptors. Ann Rev Immunol (2006) 24:419-466 (1)). In the context of a MHC-II binding groove defined as a 15 amino acid chain:

TCEM IIa exposes amino acids in pocket positions (2,3, 5,7,8) with the corresponding GEM IIa amino acids as (−3,2,−1,1,4,6,9,+1,+2,+3)

TCEM IIb exposes (−1,3,5,7,8) with the corresponding GEM IIb (−3,2,1,2,4,6,9,+1,+2,+3)

FIG. 1 illustrates the amino acid and MHC pocket position numbering scheme used herein.

It should be understood that any given peptide may comprise both TCEM which are formed by binding in MHC-I grooves and TCEM which are formed by binding in MHC-II molecule grooves; and indeed that a single peptide may comprise not only MHC-I and MHC-II TCEMs, but also can fulfill the criteria of both TCEM IIa and TCEM IIb as described above.

Any given TCEM may be combined with many different GEM to make up the entire MHC binding peptide. Which amino acids are found in the GEM positions is a function of the protein of origin, whether self or non-self. It follows that a GEM may be designed or engineered to provide a desired binding affinity. The GEM amino acids will determine binding affinity on an MHC allele and locus specific basis. Thus binding to MHC-IA and MHC-IB, and to MHC-II DR, DQ and DP alleles of MHCII all can result in higher or lower binding affinity GEMS. Such binding is also competitive relative to other excised peptides from the same protein or otherwise found in the same cellular location.

Based on these structural considerations of which amino acids determine pMHC binding affinity and which amino acids are exposed to T-cells as the obverse face of a pMHC complex, it is possible to categorize any set of peptides, irrespective of whether their source is from antibody molecules, molecules from pathogens, or from biotherapeutic molecules or any other protein. Whether a pMHC will be an upregulating or downregulating epitope, is a product of both its binding affinity (and hence dwell time) in the context of the host MHC alleles and the frequency with which T-cells have been previously exposed to that motif.

The primary function of the adaptive immune system is to differentiate self from not-self and to allow the body to mount an appropriate response to molecules, once identified as self or as not-self. This may require that there is no response to a self-antigen (tolerization) and at the other extreme a very vigorous and rapid cellular, antibody and cytokine response to an invading pathogen. Calibration of the response according to the recognition of the antigen is the product of several layers of recognition and the balance of qualitative, quantitative, and temporal stimuli.

A role of the endogenous production of antibodies is to provide a reference profile of TCEMs which calibrate the response and differentiation of self and non self. By administration of a suitable array of TCEMs it is thus possible to reinstate the balance of self discrimination and self tolerization and to provide T cell stimulation necessary to maintain a healthy T cell population responsive to exogenous antigens. The present invention has at its core the demonstration that the array of TCEMs produced in the immunoglobulin variable regions of domestic mammals is similar to that produced by humans and that the administration of TCEMs in the immunoglobulins of domestic animals can provide a functional surrogate for endogenous immunoglobulins and can assist in rebalancing the endogenous profile of TCEMs and thus ensuring a balanced population of T cells capable of self differentiation and response to exogenous epitopes.

In a related application the inventors have described a method for classification of TCEMs in proteins and the categorization of TCEMs found in human immunoglobulin variable regions.

By combining predictions of pMHC binding affinities and endosomal processing with databases of TCEM motif frequencies, it is possible to create databases to cross reference molecules from different origins in order to make predictions as to their immunogenic potential as components of vaccines, and their role as possible sources of auto-immune responses or allergic responses, or as regulatory T-cell responses.

One embodiment of the present invention is to provide a source of TCEM motifs of exogenous origin which may provide a diverse array of immunostimulation. In particular the source of TCEMs is the immunoglobulins derived from the milk, blood, or eggs of domestic animals. In a preferred embodiment the TCEM array in this exogenous source is evaluated to determine its similarity to the array of TCEMS derived from endogenous immunoglobulin variable regions.

Immune dysregulation is an increasing cause of morbidity. Among the autoimmune conditions which are increasing in incidence in the US are diabetes, systemic lupus erythematosus, chronic fatigue syndrome, rheumatoid arthritis, and celiac disease.

Autoimmune conditions which are considered potentially able to benefit from the invention described herein, in addition to the aforementioned, include celiac disease, narcolepsy, rheumatoid arthritis and multiple sclerosis (Jones, E. Y. et al, 2006. Nat. Rev. Immunol. 6:271-282.). Other autoimmune diseases include but are not limited to Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Chronic fatigue syndrome, Cogan syndrome, Cold agglutinin disease, Crohn's Disease, Dermatomyositis, Diabetes mellitus type 1, Diabetes type II, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Pemphigus vulgaris, Polymyositis, Primary biliary cirrhosis, Psoriasis, Psoriatic Arthritis, Relapsing polychondritis, Rheumatoid arthritis, systemic lupus erythematosus, Sjögren's syndrome, Temporal arteritis, Ulcerative Colitis, Vasculitis, and Wegener's granulomatosis.

In a number of instances microbial infections are known to lead to a subsequent autoimmune reaction, including, for example but not limited to, in Lyme Disease, Streptococcal infections, and chronic respiratory infections (Hildenbrand, P. et al, 2009. Am. J. Neuroradiol. 30:1079-1087; Lee, J. L. et al, Autoimmun. Rev. 10.1016 0.2009; Leidinger, P. et al Respir. Res. 10:20, 2009), Guillan Barre (Yuki N (2001) *Lancet Infect Dis* 1 (1): 29-37, Yuki N (2005) *Curr Opin Immunol* 17 (6): 577-582; Kieseier B C et al, (2004) *Muscle Nerve* 30 (2): 131-156), rheumatoid arthritis (Rashid T et al (2007) *Clin Exp Rheumatol* 25 (2): 259-267), rheumatic fever (Guilherme L, Kalil J (2009) *J Clin Immunol*), narcolepsy (de la Herrera Arita 2013(3).

The development of vaccines can result in a large population of subjects being exposed to a novel array of epitope motifs. A number of situations have arisen in which adverse immune responses to vaccines have resulted in autoimmune reactions. As one non-limiting example, Influenza vaccination has been associated with Guillan Barre disease (Vellozzi Clin Infect Dis 2014) and with narcolepsy (del a Herrera Arita 2013 (3). For many autoimmune diseases a specific epitope associated with etiology has not been identified and the underlying cause seems to be a more generalized immune dysregulation.

Another group of individuals in which immune rebalancing is needed is the immunocompromised. This group of individuals includes but is not limited to the elderly, individuals who have undergone treatment to produce immunosuppression in preparation for organ or cell transplants, and those afflicted with infections such as HIV which deplete immune cells. In these cases the repertoire of T cells needs to be rebuilt and re-trained as to the normal profile of TCEMs.

The response to vaccination may be deficient in malnourished individuals. This group of individuals includes neonates and infants especially in developing countries, in which both maternal nutrition and nutrition of the infant may not have provided a diverse array of immune exposure and have given rise to deficient or imbalanced exposure toe T cell exposed motifs. Administration of a balanced source of TCEM motifs to such subjects may assist in the development of a robust immune response following vaccination.

There is increasing recognition of the role of T cells in maintaining immunological memory. In addition to exogenous immunostimulants such as microorganisms, immunoglobulin variable regions provide a rich source of epitope diversity in priming the T cell population and generation of a broad immunological memory.

We have shown that the frequency distribution of TCEMS in human immunoglobulins provides a distinct and clearly defined frequency profile of common and rare motifs (see applications 62/023,212 and 62/047,385, each of which is incorporated herein by reference in its entirety, and Example 1 below) and have described methods for identifying and preselecting TCEMs according to their frequency profile in normal human immunoglobulin. (T Motif). The continual generation of novel immunoglobulin variable regions by endogenous B-cells, processed and presented in complex with MHC provides a continual tuning of the TCEM profile to which T cells are exposed and thus provides a means of maintaining an active T cell population responsive to a balanced frequency profile of TCEMs. It is well known that T cells are polyspecific and this appears to be determined by responsiveness to TCEM, which necessarily have a limited frequency distribution. As a pentamer can only comprise 3.2 million possible variant combinations of amino acids ($20^5$) the breadth of variation in epitopes and the downstream cytokine responses are a function of the combination of the TCEM with the GEM motifs which provide further variability and affect the affinity of binding to a MHC allele. We have shown that natural human immunoglobulins do not comprise the full array of 3.2 million TCEM but rather are limited to approximately 10% of this range (See, e.g., applications 62/023,212 and 62/047,385, each of which is incorporated herein by reference in its entirety). These appear to provide a core "self profile" of TCEM which assist in self discrimination and also provide a broadly responsive T cell community which can be polyspecific first responders to many exogenous epitopes.

While processing by B-cells of autologous immunoglobulin variable regions is an ongoing process, immunoglobulins are also taken up and processed for MHC presentation by other APCs. These include dendritic cells and macrophages. One particular source of immunoglobulins are those presented to APCs in the intestinal mucosa.

The therapeutic benefit of Intravenous immunoglobulin (IVIG) is well known and has been widely applied as an aid to immune rebalancing following immune depletion and as a therapeutic in autoimmune disease (4, 5). The mechanism of action has been poorly understood but is hypothesized to be due to the role of immunoglobulin in stimulating T cell diversity (6, 7). It has also been shown that IVIG can function orally in animal models, where immunosuppressive effects of oral IVIG are demonstrated; however these experiments have been directed towards the role of human immunoglobulin constant regions as immunosuppressives (8).

Maternal transfer of immunoglobulins has a dual role of providing specific pathogen neutralizing antibodies and also of providing an array of immunoglobulin variable regions. The former aspect of maternal immunoglobulin transfer has received most attention and these direct benefits are well documented (9). In the second scenario, the peptides in variable regions are processed by the APC of the offspring and presented in the context of the offspring's MHC alleles, only half of which are maternally derived. This assists the offspring in establishing a self-profile of TCEM frequency distribution and a corresponding T cell population. How maternal transfer of immunoglobulins is accomplished varies between species. In some species transfer is achieved by transplacental transfer of IgG while in others primarily post-natally via milk (10). In the human, and other primates, a significant level of transfer of immunoglobulins from mother to fetus occurs transplacentally, enabled by the chorioallantoic placenta. In rabbits and guinea pigs transplacental transfer also occurs. In many other species the placenta is not permissive to immunoglobulin passage and maternal offspring transfer depends entirely or mostly on immunoglobulin in milk. This is especially the case in ruminants. The colostrum of all species has a high concentration of immunoglobulin. However milk produced throughout lactation has a significant amount of immunoglobulin. Milk is therefore a rich source of immunoglobulins. While transfer of immunoglobulins from colostrum occurs, depending on species, passively via loose mucosal cell junctions which permit macromolecular transfer, after a few days and in the adult uptake of immunoglobulins is mediated via FcRn receptors and uptake by APCs in the intestinal mucosa. Intestinal digestion of immunoglobulins is slower than for other milk proteins. Gastric digestion has less impact on immunoglobulins than other milk proteins and pepsin digestion may release heavy chains from variable regions (11, 12). In adult humans about 60% of IgG is still intact at the end of the jejunum and 20% in the ileum. The intestinal lamina propria and Peyers patches are populated by dendritic cells and macrophages capable of uptake of immunoglobulin fragments or whole molecules and processing for MHC presentation.

Table 1 shows the relative concentration of immunoglobulin in bovine milk.

| Immunoglobulin | Concentration mg/Ml | | % Total immunoglobulins | |
| --- | --- | --- | --- | --- |
| | Colostrum | Milk | Colostrum | Milk |
| IgG1 | 47.6 | 0.59 | 81.0 | 73.0 |
| IgG2 | 2.9 | 0.02 | 5.0 | 2.5 |
| IgA | 3.90 | 0.14 | 7.0 | 18.0 |
| IgM | 4.2 | 0.05 | 7.0 | 6.5 |

Absolute and relative concentrations of immunoglobulins differ somewhat by species (11)

Immunoglobulins are found largely in the whey fraction of milk. Of the milk proteins, it is the immunoglobulins which comprise the highest density of peptide motifs which correspond to those found in a reference database of human immunoglobulin variable regions. In contrast alpha-lactalbumin, beta-lactoglobulin and casein have very few pentamer T-cell exposed motifs that are characteristic of those found in human immunoglobulin variable regions. The dietary benefits of milk have been well documented, including those which appear to derive from the positive impact on the immune system. However, the underlying mechanism has not been understood or documented in so far as this relates to priming of T cells by exposure to motifs from immunoglobulins presented to T cells by antigen presenting cells.

Examples of the beneficial effects of milk and colostrum are known both anecdotally and through scientific study. Among the studies reporting benefits to the immune system are the following. Consistent consumption of yogurt has been shown to reduce serum IgE levels and the occurrence of allergies (13). Colostrum has been shown to have an immunomodulatory effect on peripheral blood cells (14) apparently through T helper cell stimulation. Whey proteins have been used to treat patients with a diverse array of cancers, infections and cardiovascular disease, with reported beneficial effects (15). Many milk based products are offered as the base for pre and probiotics; however there is often a failure to separate the effect of the milk from that of the microbial culture (16). The benefits of oral exposure to bovine immunoglobulins have also been shown to extend to dogs and to enhance titer and duration of vaccine immunoglobulin responses (17), presumably by priming and enhancement of a helper T cell response enabling higher antibody titers to be achieved. In none of these studies however has there been an attempt to relate the beneficial effects observed to the array of T cell exposed motifs presented by MHC.

TABLE 2

| | Line 1 | Line 2 | P-value |
| --- | --- | --- | --- |
| IgY levels[1] | | | |
| Dams' plasma[2] (mg/mL) | 3.26 ± 0.22[b] | 6.02 ± 0.40[a] | <0.0001 |
| Egg yolk total[3,4] (mg) | 22.5 ± 0.70[b] | 43.9 ± 0.73[a] | <0.0001 |
| Egg yolk[3,4] (mg/mL) | 1.15 ± 0.03[b] | 2.26 ± 0.03[a] | <0.0001 |
| Egg white total[3,4] (µg) | 128 ± 9.44[b] | 354 ± 17.7[a] | <0.0001 |
| Egg white[3,4] (µg/mL) | 3.57 ± 0.27[b] | 9.88 ± 0.50a[a] | <0.0001 |
| IgA levels[1] | | | |
| Dams' plasma[2] (µg/mL) | 301 ± 30.8 | 346 ± 30.4 | 0.3050 |
| Egg yolk total[3,4] (µg) | 305 ± 13.7[b] | 428 ± 17.0[a] | <0.0001 |
| Egg yolk[3,4] (µg/mL) | 15.5 ± 0.68[b] | 22.1 ± 0.85[a] | <0.0001 |
| Egg white total[3,4] (µg) | 257 ± 11.5[b] | 493 ± 13.7[a] | <0.0001 |
| Egg white[3,4] (µg/mL) | 7.06 ± 0.30[b] | 13.7 ± 0.35[a] | <0.0001 |
| IgM levels[1] | | | |
| Dams' plasma[2] (µg/mL) | 859 ± 30.4[b] | 975 ± 35.6[a] | <0.0210 |
| Egg yolk total[3,4] (µg) | 387 ± 14.4 | 413 ± 14.8 | 0.2157 |
| Egg yolk[3,4] (µg/mL) | 19.7 ± 0.68 | 21.3 ± 0.750 | 0.1248 |
| Egg white total[3,4] (µg) | 207 ± 6.65[b] | 249 ± 6.55[a] | <0.0001 |
| Egg white[3,4] (µg/mL) | 5.67 ± 0.16[b] | 6.87 ± 0.16[a] | |

Immunoglobulin content of plasma, egg yolk and egg white in two lines of chickens. Adapted from Hamal et al 2006 Poultry Science 85:1364-1372

We have shown (Example 2) that the TCEM frequency profile found in the immunoglobulins of many animals is very similar to that of humans. It follows that milk, blood or eggs of several domestic species can be used as a source of defined and balanced TCEMs in much the same way as IVIG. Further, plasma from domestic animal species carries immunoglobulins which can provide a similar balanced profile of TCEMs. Thus the immunoglobulins from milk, blood, or eggs of domestic mammals are a good source of a diversity of TCEM containing peptides like those in human immunoglobulins.

In one embodiment therefore, the present invention focuses on the use of domestic animal immunoglobulins as a source of protein compositions which have a known frequency distribution of TCEMs, wherein said frequency distribution of TCEM is similar to that of a reference database of TCEM derived from human immunoglobulins. In some embodiments domestic animal immunoglobulins are derived from milk; in yet other embodiments said immunoglobulins are derived from blood. In further embodiments, the immunoglobulins are derived from eggs. The milk which is the source of immunoglobulins may be from cow, buffalo, sheep, goat, camel, or horse or any other domestic animal which is customarily milked for human consumption. In some instances the immunoglobulin is harvested from whole milk; in 1 harvested from colostrum. In preferred embodiments the TCEM profile of the harvested milk product is determined and compared to that of the reference database of human immunoglobulin variable regions to compare the frequency profile of TCEMs. In further preferred embodiments the milk derived immunoglobulin containing product is analyzed to determine the concentration of TCEMs in the prepared product.

The milk product is prepared with consideration to the preservation of immunoglobulins and in particular the immunoglobulin variable regions. Such preparation may include fractionation, concentration and treatment to remove pathogens. Immunoglobulins in milk have been shown to be reasonably tolerant of pasteurization but are severely damaged by ultra-heat treatment (UHT) (9). Fermentation of milk sugars resulting in acidification does not significantly damage immunoglobulins.

In yet other embodiments the immunoglobulins may be harvested from the blood of domestic animals. In preferred embodiments blood is collected at slaughter of cattle, sheep, goats, pigs, rabbits, or horses or any other species in which large scale collection of blood products is feasible. In preferred embodiments the TCEM profile of the harvested blood product is determined and compared to that of the reference database of human immunoglobulin variable regions to compare the frequency profile of TCEMs.

In yet further embodiments, the immunoglobulins may be harvested from eggs of domestic poultry. In preferred embodiments, the TCEM profile of the harvested egg product is determined and compared to that of the reference database of human immunoglobulin variable regions to compare the frequency profile of TCEMs.

The present invention addresses the methods for determination of TCEM composition in milk, eggs and blood of domestic animal sources and comparison of the frequency profile by comparison with a pre-established reference database of TCEMs in human immunoglobulin variable regions.

Preparations of immunoglobulin from domestic animal sources comprising the desired TCEM profile are, in one preferred embodiment, administered orally. Oral administration of said immunoglobulins comprising a determined TCEM profile may be as a nutritional supplement or as a pharmaceutical product. When delivered as a nutritional enhancement the products may be included in a fermented milk product such as yogurt or kefir. In yet other embodiments a fluid product that is not fermented may be used. Alternatively they may be administered as a whey derived product or concentrate. The nutritional enhancement maybe blended into other dairy products to increase the content of immunoglobulins. In yet other embodiments the palatability may be enhanced by flavoring or sweetening. When delivered as a pharmaceutical product comprising a determined TCEM profile the immunoglobulin derived product may be administered orally as a fluid or as a concentrate in capsules or pills and may be further modified to improve palatability.

In a further embodiment, the desired composition of TCEM is achieved in the presence of food fermentation bacteria, including but not limited to bacteria such as *Lactobacillus, Streptococcus* or *Bifidobacterium* species. Bacterial proteases can bring about partial cleavage of the immunoglobulins to render the TCEM more accessible to antigen presenting cells. Other bacteria digest other milk proteins but have no effect on immunoglobulins and immunoglobulin maintains its structure intact. By fermentation of lactose the fermentation bacteria reduce the pH and may also assist in preserving immunoglobulins and immunoglobulin polypeptides and the TCEM arrays they contain. In a particular embodiment the combination of a dairy product with a probiotic culture may achieve the delivery of an array of immunoglobulins and partially cleaved immunoglobulins comprising a particular combination of TCEM that bring about immune balancing.

In yet other embodiments immunoglobulins derived from domestic animal milk, eggs or blood, and in particularly preferred embodiments the immunoglobulin variable regions only, and having a desired profile of TCEMs, may be prepared for administration by other routes including parenterally.

In further embodiments, a formulation is prepared containing a known concentration of domestic animal immunoglobulins and the peptide and polypeptide derivatives thereof and prepared for oral delivery. In preferred embodiments said oral delivery is in the form of a capsule or tablet. In yet other formulations said delivery is as a liquid suspension or solution or as or powder or granules. Such formulations may be incorporated into enriched dairy products of milk or fermented milk or may be incorporated in to a gel or gum based product to make the dosage a chewable form. The oral formulation may, in one embodiment be delivered as a drink or beverage, while in other embodiments it is delivered as a functional food. In some preferred embodiments the oral delivery is to a young child or baby while in other embodiments the formulation is suitable for an adult and in particular, for the elderly.

In particular embodiments the oral administration of domestic animal immunoglobulin fractions of known concentration may also contain shorter peptide and polypeptide chains derived from immunoglobulins. The immunoglobulin polypeptide fraction may be mixed with probiotic bacteria.

A particularly desirable use of the oral formulation of domestic animal immunoglobulins of known concentration is in enhancing the immune response of a subject. In some embodiments the oral formulation may be administered in advance of vaccination in order to enhance the immune response. In yet other embodiments the oral formulation is administered to subjects with immune imbalances which have arisen as the result of autoimmune disease, infections, cancer, or therapy by transplantation or chemotherapy.

No special preparation of the donor animals is required; the immunoglobulin polypeptide fraction in the oral formulation may be prepared from bulk milk, plasma or eggs. Indeed it is desirable that the immunoglobulins are harvested from a wide diversity of individual donor animals and that no special preimmunization or hyperimmunization of said animals should have occurred.

EXAMPLES

Example 1: Establishment of a Reference Database of Human Immunoglobulin Derived TCEMs A. Assembly of Motifs in Immunoglobulin Variable Regions as a Reference Database As of December 2013, Genbank contained approximately 45,000 sequences identified as immunoglobulin heavy variable regions (IGHV) and for which the repository metadata records did not contain indications that they were derived from individuals with immunopathology. Some sequences were submitted in conjunction with specific publications; others were direct submissions. The majority do not indicate a source molecule isotype. Genbank does not provide a means to identify and link sequence submissions in the database for heavy and light chain immunoglobulins from the same molecule. In some cases these can be deduced from accession numbers. There are 3-4 times as many IGHV as IGLV regions in Genbank databases, likely due to the technical difficulties of light chain sequence extraction due to so-called aberrant light chains. We therefore elected to focus on the IGHV.

Approximately 45,000 heavy chain variable regions were retrieved from NCBI Protein resource with a search argument "(immunoglobulin heavy chain variable region) AND (*homo sapiens*)". The numbers of IGHV greatly outnumber the number of light chain sequences. In addition, because of the way proteins are deposited and annotated the heavy chain and light chain variable region pairs are not explicitly connected. Therefore only IGHV sequences were used in the current analysis. Various restrictive combinations of search arguments were used to create non-redundant subsets of this larger set that were either immunoglobulin class-defined or for which the metadata attached to the accession indicated that they were associated with an immunopathology. Additionally, manual curation was used to remove sequences that were obviously not immunoglobulins. The final dataset thus included approximately 40,000 (n=39,957) non-class-defined immunoglobulins. As the resulting dataset comprises many different accession groups from studies carried out over a considerable period of time it can be considered a representative sample of the gamut of "natural" human immunoglobulins. Accessions with signal peptides were identified and removed from the input sequences using the combined signal peptide and transmembrane predictor Phobius (phobius.sbc.su.se). IGHV were included in the final set if they contained at least 80 amino acids, a value approximating the shortest germline equivalent sequence. All sequences longer than 130 amino acids were truncated at that point. To assist the reader the approximate positions of the three complementarity determining regions (CDR) have been indicated in FIG. 1 relative to standard IGHV sequence landmarks.

Class-defined IGHV sets of IgG (n=1630), IgE (n=667), and IgM (n=537) were derived similarly by adding additional key words to the search arguments. There are inevitable biases in the class-defined datasets. For example the sources of nearly all of the IgE sequences were from cohorts of asthmatics (18-20) and either did not include or identify the sequences of non-asthmatics in the cohorts. Likewise the IgG sequences were derived from an HIV study (21). Germline IGHV (n=161) were obtained from the IMGT repository (www.imgt.org), and immunoglobulin heavy chain constant regions (IGHC) class reference sequences from Genbank. Additional database collections were assembled including Commercial biotherapeutic sequences (IMGT.org repository); these numbered 163. Ig sequences where the secondary annotations specified derivation from an immunopathology were assembled by a Genbank query. These numbered approximately 4000.

The human proteome, exclusive of immunoglobulins, was downloaded from www.uniprot.org comprising approximately 81,000 proteins which includes multiple isoforms of some proteins.

These datasets were used as reference series for comparison of the binding patterns, determination of motif frequencies, and comparison of proteins of interest.

B. Extraction and Scoring of Motifs in Human Immunoglobulin Variable Regions

For each of the analyses described below each sequence in the derived databases was broken into 15-mers and 9-mers, each offset by a single amino acid. Thus, the combined set of 40,000 IGHV sequences resulted in approximately $4.2 \times 10^6$ peptides. The same manipulations were carried out with the IGHV germline sequences, immunoglobulin constant regions, and the human proteome.

For each derived 9-mer and 15-mer peptide, the predicted binding affinity to 37 MHC I and 28 MHC II alleles was determined. This was done using methods previously described (22). Briefly, the principal components of physical properties of each amino acid were derived from a large set of published data. The first three principal components account for approximately 90% of the variability. For a peptide a matrix is constructed consisting of the descriptors for each of the constituent amino acids. Binding affinity datasets for the MHC I and MHC II alleles were obtained from IEDB (www.iedb.org) and used as training sets for neural network development (NN). Amino acid sequences of the peptides were converted to principal component matrices and a bootstrap aggregation "bagging" process was used with the training sets to produce ensembles of NN equations for each of the alleles (23, 24). The ensemble approach enables the computation of a predicted mean and variance of affinity for each component peptide. Predictions for each MHC for each protein will exhibit a unique distribution binding affinities. Thus for computations consisting of either binding affinities for a number of alleles or a number of different proteins the predicted mean affinities for each allele are standardized to zero mean and unit variance. This standardization is done within protein using a Johnson Sb algorithm (JMP platform) and the predictions for the protein reported in standard deviation units.

The probability of cleavage of each protein by human cathepsin B, L, or S was determined using methods previously described. Briefly, matrices of the amino acid principal components were derived as outlined above for a cleavage site octomer (CSO). By convention the scissile bond is between amino acids 4 and 5 of the CSO and is described as P1P1'. Large proteomic data sets of cleavage by the three cathepsins were used to produce the input cleavage training sets for development of a NN binary classifiers (25-27). Bagging was used to create the ensemble predictors and the median of the probabilities of the predictive equation ensembles is used as the probability of scissile bond cleavage of a CSO. The accuracy of the predictors varies for the different cathepsins and for different P1P1' dipeptides. The overall median AROC for the classifiers is 0.87. Using this process a probability of cleavage by the each of cathepsins was computed for all possible octomers indexed by single amino acids from each immunoglobulin.

It should be noted that there is a substantial cellular tropism to cathepsin expression and not all APC have the same profile of cathepsins; B cells do not express cathepsin L. We have examined and have found a good overall concordance across a variety of published endosomal cleavage datasets such as CLIP processing (28) and display of self peptides (29).

We extracted datasets of TCEM and GEM motifs from all 40,000 curated IGHV proteins. This was done by creating sets of 15-mer motifs, and then the corresponding sets of TCEM for MHC-I TCEM and MHC-II TCEMa and TCEMb, in which the different relevant TCEM positions given their amino acid, while non-TCEM positions were replaced by a standard non-amino acid code ("~") or an X. In this way it is possible using standard relational algebra of sets to extract replicated TCEMs as well as determining their frequencies of occurrence and their affiliated GEM binding affinity characteristics.

15-mers with their associated TCEM and GEM were generated from all downloaded sequences.

We initially applied uTOPE™ MHC Binding affinity prediction analysis (see, e.g., PCT US2011/029192, PCT US2012/055038, US2014/01452, and US2014/041525, each of which is incorporated herein by reference) to a subset of the IGHV sequences. Because of computational resource limitations we initially did a full MHC binding prediction predictions on approximately a third of the 40K set (14 K sequences). Some figures provided herein are based on this initial subset. Having now completed the processing of the complete dataset no significant differences are seen in the figures, or in the conclusions drawn from the subset vs the whole dataset.

Motif Extraction

Each of the mature somatic hypermutated (SHM) IGHV sequences comprise approximately 120 amino acids (without signal peptides) and thus produce approximately 110 motifs. Thus, the 40,000 IGHV proteins produced about $4.4 \times 10^6$ peptides each having 3 different potential TCEM configurations. As any one discontinuous pentamer motif can have $20^5$ different configurations, or 3.2 million, 9.6 million total potential motifs exist in the following three possible configurations:
1. MCH IIA (2,3,5,7,8) as 15-mer
2. MHC IIB (−1,3,5,7,8) as 15-mer
3. MHC I (4,5,6,7,8) as 9-mer We observed that there is a high level of motif re-use within the IGHV. Each of the 3 sets consisted of only approximately 275,000 unique motif sequences and thus there was significant motif re-use in different molecules. The motif usage frequencies were found to follow a power law (Pareto) distribution characteristic of network ensembles, as shown in Table 3.

TABLE 2

| FC TCR II (−1, 3, 5, 7, 8) | N Rows | Mean(N TCR II (−1, 3, 5, 7, 8), Germline) | Mean(N TCR II (−1, 3, 5, 7, 8), Mutated) |
|---|---|---|---|
| 1 | 8 | 25,710 | |
| 2 | 56 | 15,205 | 13,919 |
| 3 | 43 | 6,453 | 6,022 |
| 4 | 140 | 3,683 | 3,417 |
| 5 | 215 | 1,715 | 1,639 |
| 6 | 500 | 908 | 878 |
| 7 | 571 | 451 | 430 |
| 8 | 1,136 | 225 | 215 |
| 9 | 1,853 | 115 | 110 |
| 10 | 3,146 | 61 | 54 |
| 11 | 6,372 | 29 | 27 |
| 12 | 12,592 | 14 | 13 |
| 13 | 24,279 | 7 | 6 |
| 14 | 34,571 | 4 | 3 |
| 15 | 55,298 | 2 | 2 |
| 16 | 135,960 | 1 | 1 |

Motifs of germline origin were processed in the same manner as the non-germline somatically hypermutated set above. The pattern of usage of germline-origin motif sequences were found to follow a similar distribution pattern. Pareto distributions are found in a wide variety of physical and biological systems and tend to exhibit linear behavior over many orders of magnitude. As is common when dealing with systems displaying this distribution pattern a logarithmic (log base 2) frequency categorization scheme was developed. As the cellular interactions between T-cells and antigen presenting cells displaying the motifs in MHC molecules on their surfaces are the ultimate result of the molecular interactions, using a log base 2 system implies that each adjacent frequency class would double or halve the cellular interactions with that motif. Thus using such a frequency categorization scheme makes it possible to characterize subtle differences in motif usage as well as providing a comprehensible way of visualizing the cellular interaction dynamics with the different motifs. Overall, the variable regions were found to comprise approximately equal numbers of germline-origin and somatic hypermutated sequences.

When both the SHM and Germline motif sets were extracted, each of the TCEMs were assigned unique identifier keys which indicated their genetic origin and frequency classification. The identifier keys are essential for carrying out the set algebra manipulations to identify and characterize the TCEMs in different protein molecules.

Thus, relational set algebra manipulation of the combined SHM and germline TCEMs using the keys assigned in combination with a protein sequence of any origin can be used to characterize all of the motifs in a particular protein into three groups as being of SHM-origin, of germline-origin, or of neither. In addition, the frequency classification scheme provides insights into how T-cells will react to sequences in the proteins of interest.

The 40K database of immunoglobulin heavy chain variable region is taken to represent the "normal" situation, but in this database the depositors of the sequences did not identify (or they may not have known) the isotype origin of the antibody molecule. However in some cases the depositors included additional metadata with the Genbank sequence accession. Thus, a further set of databases were created using metadata in the accession records of the Genbank sequences. In particular, two broad categories of sequences were identified: one set comprised antibody molecules that were isotype identified (IgG, IgE, IgM) and a second set comprised antibody molecules associated with several different immunopathologies. Immunopathologies such as rheumatoid arthritis, lupus erythematosus, leukemia, lymphoma and the like are generally characterized by abnormal T-cell and B-cell interactions. The metadata was further curated to create unique, non-redundant sets of molecules. Subsets were created for IgG, IgE, IgM, lupus erythematosus (SLE), rheumatoid arthritis, chronic lymphocytic leukemia, lymphoma, and multiple sclerosis. Further curation was necessary because the original Genbank sometimes metadata associated more than one immunopathology with a particular antibody molecule. In total, these further curated subsets comprised approximately 8,000 molecules with individual subsets ranging from 200 molecules to 3000 IGHV sequences. These sequences were categorized for motifs as described above.

The human proteome database comprised approximately 81,000 proteins. This includes multiple isoforms of many proteins, hence the 81,000 exceeds the total proteome of any one human being. The proteome consists of about twice as many proteins as the IGHV database, but their average size is considerably larger than that of the IGHV. When decomposed into their composite 15-mer peptides each indexed by one amino acid this resulted a total of 33 million peptides. When processed similarly to described above this produced about 2.42 million unique motifs, comprising about 7.5 million unique motif sequences in aggregate for the three motif configurations. As expected, IGHV-origin motifs were found in the proteome. The 275,000 motifs of IGHV-origin were found to match approximately 10% of the human proteome motifs. Thus, a database of IGHV sequences ten times the size of the current should provide complete coverage for all motifs in the human proteome. The total B-cell clones in a human exceed $10^7$ and thus the full B-cell population provides full coverage of the human proteome. In addition, it was found that about 15% of the IGHV-origin motifs had no matches in the human proteome thus giving credence to the concept that the IGHV provides a broad training of the immune system even for proteins foreign to the body.

Database Assembly

The datasets resulting from the above processes were designed to be analyzed and manipulated within JMP® (SAS Inc., Raleigh N.C.) using tools that combine relational set algebra with statistical analysis. In particular, the sets were created so that a set JOIN operation with any protein or group of proteins (for example a virus, a bacteria, a biotherapeutic) would enable the identification of matching motifs between the sets.

For Example:
JOIN-ing the motif sequences from influenza H1N1 with the 40K IGHV motif sequence dataset identified a set of motif sequences present in both the virus and the antibody molecules and which had a characteristic binding pattern with a clinically relevant MHC HLA. A further JOIN with the human proteome identified a specific subset of proteins that also contained the same motif and further identifies motifs from other human proteins of non-immunoglobulin origin that likewise share motifs with the virus.

However this is not considered limiting and alternative computer programs may be used to derive and process the datasets.

Example 2. Determination of the TCEM Profiles in Non-Human Species

Heavy chain variable regions were retrieved from NCBI Protein resource with a search argument "(immunoglobulin heavy chain variable region) AND (species latin name)", where "species latin name" was the designation of each species of animal. Species included are shown in Table 3 along with the number of heavy chain variable regions accessed.

Example 3: Frequency Distribution of TCEMs in Bovine Compared to Human

TCEM IIa motifs were extracted from the 221 bovine IGHV sequences, accessed as described in Example 2, and a histogram created of the frequency of use of each of the different motifs. This process is the same as was used for the 40K database that is nearly 200× as large. As shown in Example 1 there is a 74% overlap in the TCEM IIa frequency of use between the bovine and human. Using the log base 2 frequency classification of the TCEM use a correlation between the frequency classes between the bovine and human datasets could be derived despite the differences in size of the dataset. The result of this analysis indicates that not only is there a highly concordant motif usage between the bovine and human but there is also a very similar frequency pattern of the overlapping motifs.

Example 4: Absence of Cleavage of Bovine Immunoglobulins by Food Fermentation Bacteria Medium was prepared consisting of protein-free mammalian cell culture medium that contains a mixture of all growth materials needed for cellular growth. Lactose was added to this media to a final concentration of 5%. Lyophilized bovine immunoglobulins were added to a final

TABLE 4

| Species | Common Name | Number of IGHV accessed from Genbank | Number of TCEM pentamers examined | TCEM IIa Overlap with human |
|---|---|---|---|---|
| Macaca mulata | Rhesus macaque | 1295 | 153476 | 0.91 |
| Rattus | Rat | 501 | 45571 | 0.91 |
| Ovis | Sheep | 66 | 8539 | 0.84 |
| Vicugna | Vicuna | 132 | 13131 | 0.84 |
| Aotus | Night or Owl monkey | 51 | 4300 | 0.82 |
| Camellus dromedarius | Dromedary | 337 | 36496 | 0.82 |
| Macaca fasicularis | Cynomolgous macaque | 59 | 7127 | 0.82 |
| Callithrix_ | Marmoset | 106 | 13665 | 0.81 |
| Canis | Dog | 194 | 20849 | 0.79 |
| Felis | Cat | 98 | 12586 | 0.79 |
| Sus | Swine | 272 | 31368 | 0.79 |
| Lama | Llama | 493 | 52178 | 0.78 |
| Papio | Baboon | 28 | 3628 | 0.78 |
| Monodelphis | Opossum | 54 | 6305 | 0.77 |
| Capra | Goat | 21 | 3020 | 0.76 |
| Bos taurus | Bovine | 221 | 28622 | 0.74 |
| Equus | Horse | 314 | 39207 | 0.73 |
| Camellus bactrianus_ | Bactrian camel | 77 | 9319 | 0.72 |
| Platypus | Duckbill platypus | 36 | 3949 | 0.72 |
| Gallus | Chicken | 57 | 6611 | 0.67 |

Figure 3:
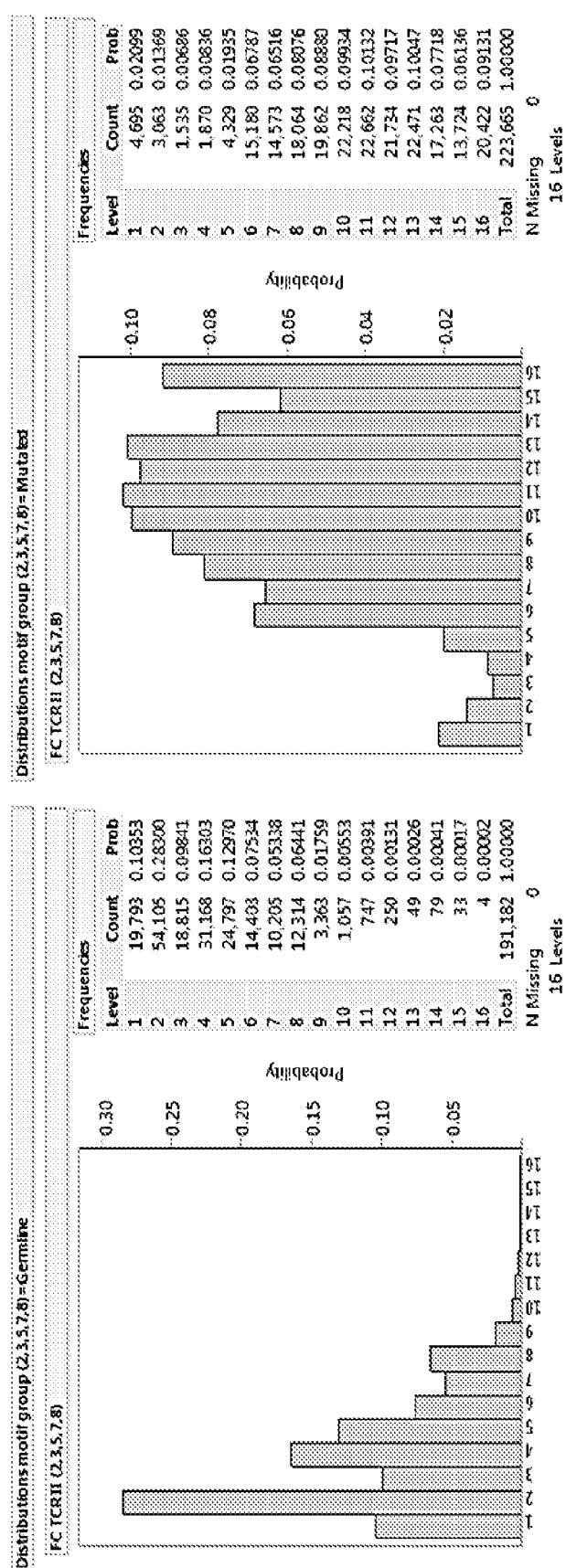
Figure 4:
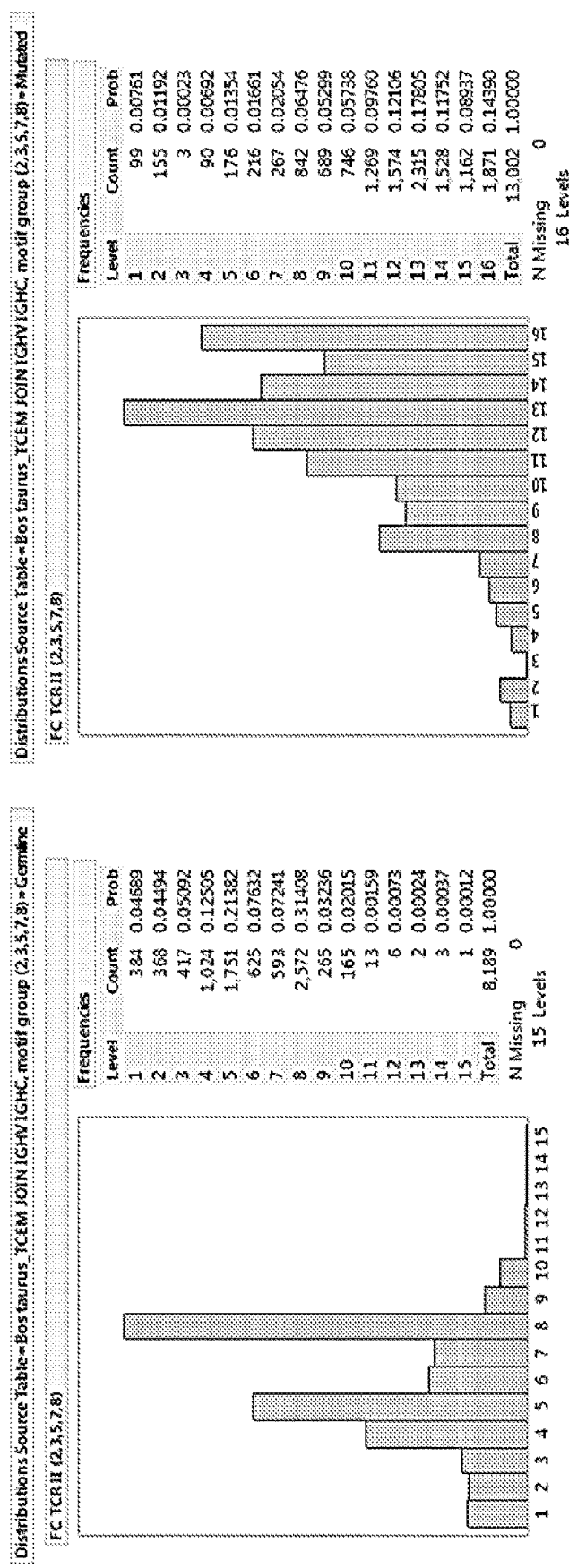

The extent of overlap of TCEMs found in the species immunoglobulins that are also found in the 40K human variable region database is shown in the last column of the table. The distribution of TCEMs across frequency classes for all animals and for bovines is shown in FIGS. 3 and 4.

IGHV of mice accessed from Genbank, comprising approximately 4000 sequences, were previously analyzed and found to have an approximately 30% overlap of TCEM II with humans. However, this species is excluded as the dataset is very biased by the predominance of only one or two inbred strains which are represented in the dataset. Balb/c mice have been consistent outliers in all observations of MHC II DRB binding.

concentration of 0.5 mg/ml. This combination thereby simulates the approximate content of immunoglobulins and lactose in whey. Probiotic bacteria (YG-3097-PL-ABY653, GetCulture. Inc) were added to this solution (0.34 mg/ml) and incubated at a temperature of 37 C to initiate the fermentation. At various times after the reaction was started the fermentation mixture was centrifuged at (6000×g) to remove the bacteria and the supernatant was prepared for SDS gel electrophoresis to estimate whether protein lysis had occurred and to identify the appearance of any immunoglobulin subproducts. Results are shown in FIG. 6.

After incubation with a mixed fermentation culture for up to 92 hours at 37 degrees almost no digestion of the immunoglobulin was observed. During this time the pH in cultures containing the probiotic cultures dropped to 4.5. The immunoglobulin heavy and light chain are observed to be intact after this treatment.

REFERENCE LIST

1. Rudolph M G, Stanfield R L, & Wilson I A (2006) How TCRs bind MHCs, peptides, and coreceptors. *Annu Rev Immunol* 24:419-466.
2. Lefranc M P, et al. (2009) IMGT, the international ImMunoGeneTics information system. *Nucleic acids research* 37(Database issue):D1006-1012.
3. De la Herran-Arita A K, et al. (2013) CD4+ T Cell Autoimmunity to Hypocretin/Orexin and Cross-Reactivity to a 2009 H1N1 Influenza A Epitope in Narcolepsy. *Science translational medicine* 5(216):216ra176.
4. Costa N, et al. (2013) Broadened T-cell repertoire diversity in ivIg-treated SLE patients is also related to the individual status of regulatory T-cells. *Journal of clinical immunology* 33(2):349-360.
5. Pires A E, et al. (2010) Treatment with polyclonal immunoglobulin during T-cell reconstitution promotes naive T-cell proliferation. *J Immunother* 33(6):618-625.
6. Joao C (2007) Immunoglobulin is a highly diverse self-molecule that improves cellular diversity and function during immune reconstitution. *Medical hypotheses* 68(1):158-161.
7. Joao C, Ogle B M, & Geyer S (2006) Immunoglobulin promotes the diversity and the function of T cells. *European journal of immunology* 36(7):1718-1728.
8. Maier E, et al. (2007) Induction of immune tolerance by oral IVIG. *International immunopharmacology* 7(3):351-359.
9. Hurley W L & Theil P K (2011) Perspectives on immunoglobulins in colostrum and milk. *Nutrients* 3(4):442-474.
10. Pentsuk N & van der Laan J W (2009) An interspecies comparison of placental antibody transfer: new insights into developmental toxicity testing of monoclonal antibodies. *Birth defects research. Part B, Developmental and reproductive toxicology* 86(4):328-344.
11. Hurley C K, et al. (1999) A special report: histocompatibility testing guidelines for hematopoietic stem cell transplantation using volunteer donors. Quality Assurance and Donor Registries Working Groups of the World Marrow Donor Association. *Human immunology* 60(4):347-360.
12. Zhang O et al. (2014) Differential digestion of human milk proteins in a simulated stomach model. *Journal of proteome research* 13(2):1055-1064.
13. Van de Water J, Keen C L, & Gershwin M E (1999) The influence of chronic yogurt consumption on immunity. *The Journal of nutrition* 129(7 Suppl):1492S-1495S.
14. Biswas P, et al. (2007) Immunomodulatory effects of bovine colostrum in human peripheral blood mononuclear cells. *New Microbiol* 30(4):447-454.
15. Marshall K (2004) Therapeutic applications of whey protein. *Alternative medicine review: a journal of clinical therapeutic* 9(2):136-156.
16. de Vrese M & Schrezenmeir J (2008) Probiotics, prebiotics, and synbiotics. *Advances in biochemical engineering/biotechnology* 111:1-66.
17. Satyaraj E, et al. (2013) Supplementation of diets with bovine colostrum influences immune function in dogs. *The British journal of nutrition* 110(12):2216-2221.
18. Kerzel S, Rogosch T, Struecker B, Maier R F, & Zemlin M (2010) IgE transcripts in the circulation of allergic children reflect a classical antigen-driven B cell response and not a superantigen-like activation. *J Immunol* 185(4):2253-2260.
19. Davies J M & O'Hehir R E (2004) VH gene usage in immunoglobulin E responses of seasonal rhinitis patients allergic to grass pollen is oligoclonal and antigen driven. *Clin Exp Allergy* 34(3):429-436.
20. Snow R E, Djukanovic R, & Stevenson F K (1999) Analysis of immunoglobulin E VH transcripts in a bronchial biopsy of an asthmatic patient confirms bias towards VH5, and indicates local clonal expansion, somatic mutation and isotype switch events. *Immunology* 98(4):646-651.
21. Bowers E, et al. (2014) Decreased mutation frequencies among immunoglobulin G variable region genes during viremic HIV-1 infection. *PloS one* 9(1):e81913.
22. Bremel R D & Homan E J (2013) Recognition of higher order patterns in proteins: immunologic kernels. *PloS one* 8(7):e70115.
23. Greenbaum J, et al. (2011) Functional classification of class II human leukocyte antigen (HLA) molecules reveals seven different supertypes and a surprising degree of repertoire sharing across supertypes. *Immunogenetics* 63(6):325-335.
24. Wang P, et al. (2008) A systematic assessment of MHC class II peptide binding predictions and evaluation of a consensus approach. *PLoS. Comput. Biol.* 4(4):e1000048.
25. Tholen S, et al. (2011) Contribution of cathepsin L to secretome composition and cleavage pattern of mouse embryonic fibroblasts. *Biol.Chem.* 392(11):961-971.
26. Biniossek M L, Nagler D K, Becker-Pauly C, & Schilling O (2011) Proteomic identification of protease cleavage sites characterizes prime and non-prime specificity of cysteine cathepsins B, L, and S. *J.Proteome.Res.* 10(12):5363-5373.
27. Impens F, et al. (2010) A quantitative proteomics design for systematic identification of protease cleavage events. *Mol. Cell Proteomics.* 9(10):2327-2333.
28. Chicz RM, et al. (1993) Specificity and promiscuity among naturally processed peptides bound to HLA-DR alleles. *J Exp Med* 178(1):27-47.
29. Costantino C M, Spooner E, Ploegh H L, & Hafler D A (2012) Class II MHC self-antigen presentation in human B and T lymphocytes. *PloS one* 7(1):e29805.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A protein product comprising an immunoglobulin polypeptide fraction derived from a milk product of a domestic animal, wherein said immunoglobulin polypeptide fraction comprises a frequency of representation of at least 60% of the T-cell exposed motifs found in a reference database of T-cell exposed motifs selected from the group consisting of T-cell exposed motifs found in human germline immunoglobulin variable region sequences, T-cell exposed motifs found in somatically mutated human immunoglobulin variable region sequences and T-cell exposed motifs found in immunoglobulin constant chains,
  wherein said reference database comprises at least 40,000 unique T-cell exposed motifs,
  wherein said immunoglobulin polypeptide fraction is formulated as a liquid and
  wherein said immunoglobulin polypeptide fraction further comprises greater than about 25% w/w immunoglobulin polypeptides, wherein w/w is the weight of the immunoglobulin polypeptides per the total weight of the fraction on a dry basis.

2. The protein product of claim 1 wherein said milk product is whole milk.

3. The protein product of claim 1 wherein said milk product is whey.

4. The protein product of claim 1 wherein said product is formulated for oral administration.

5. The protein product of claim 1 wherein said product is formulated as a composition selected from the group consisting of a nutritional supplement and a pharmaceutical product.

6. The protein product of claim 1, wherein said protein product is formulated as an infant formula.

7. The protein product of claim 1 wherein at least 70% of said T cell exposed motifs are found in said reference database.

8. A method of enhancing the immune response of a subject, improving response to vaccination, stimulating the cellular immune system, modulating the cellular immune system, enhancing resistance to infection, mitigating suffering resulting from an immune imbalance, mitigating suffering resulting from an immunopathology, or mitigating suffering resulting from allergy, comprising administering to said subject the protein product according to claim 1.

9. The method of claim 8 wherein said subject is a companion animal or a livestock animal.

10. An oral formulation comprising an immunoglobulin polypeptide fraction derived from a domestic animal, wherein said immunoglobulin polypeptide fraction comprises a frequency of representation of at least 60% of the T-cell exposed motifs found in a reference database of T-cell exposed motifs selected from the group consisting of T-cell exposed motifs found in human germline immunoglobulin variable region sequences, T-cell exposed motifs found in somatically mutated human immunoglobulin variable region sequences and T-cell exposed motifs found in immunoglobulin constant chains, wherein said reference database comprises at least 40,000 unique T-cell exposed motifs,
  said immunoglobulin polypeptide fraction further comprising greater than about 25% w/w immunoglobulin polypeptides, wherein w/w is the weight of the immunoglobulin polypeptides per the total weight of the fraction on a dry basis, and
  wherein said oral formulation is selected from the group consisting of a powder, a liquid, a capsule and a gel.

11. The oral formulation of claim 10, wherein said immunoglobulin polypeptide fraction comprises greater than about 75% w/w immunoglobulin polypeptides, wherein w/w is the weight of the immunoglobulin polypeptides per the total weight of the fraction on a dry basis.

12. The oral formulation of claim 10, wherein said oral formulation is configured to provide from 0.1 to 10.0 grams of said domestic animal immunoglobulin fraction per dose.

13. The oral formulation of claim 10, wherein said oral formulation is a functional food.

14. The oral formulation of claim 10, wherein said immunoglobulin fraction has been partially digested by proteases.

15. The oral formulation of claim 10, wherein said oral formulation comprises immunoglobulin fragments.

16. The oral formulation of claim 10, wherein said domestic animal immunoglobulin fraction has been prepared from animals that have not been hyperimmunized.

17. The oral formulation of claim 10, wherein said domestic animal immunoglobulin fraction is a bulk immunoglobulin fraction.

18. The oral formulation of claim 17, wherein said bulk immunoglobulin fraction has not been processed to enrich an immunoglobulin that binds to a particular antigen.

* * * * *